US008088590B2

(12) United States Patent
Mani et al.

(10) Patent No.: US 8,088,590 B2
(45) Date of Patent: Jan. 3, 2012

(54) USE OF FOXC2 IN DIAGNOSING, PREVENTING AND TREATING CANCER METASTASIS

(75) Inventors: Sendurai Mani, Cambridge, MA (US);
Jing Yang, Cambridge, MA (US);
Robert A. Weinberg, Brookline, MA (US)

(73) Assignee: Whiteland Institute for Biomedical Research, Cambridge, MA (US)

( * ) Notice: Subject to any disclaimer, the term of this patent is extended or adjusted under 35 U.S.C. 154(b) by 1352 days.

(21) Appl. No.: 11/646,706

(22) Filed: Dec. 28, 2006

(65) Prior Publication Data

US 2010/0260827 A1 Oct. 14, 2010

Related U.S. Application Data

(63) Continuation of application No. 11/090,437, filed on Mar. 25, 2005, now abandoned.

(60) Provisional application No. 60/556,726, filed on Mar. 26, 2004.

(51) Int. Cl.
*G01N 33/574* (2006.01)
*C12Q 1/68* (2006.01)
(52) U.S. Cl. .............................. 435/7.23; 435/6; 435/7.1
(58) Field of Classification Search .................... None
See application file for complete search history.

(56) References Cited

U.S. PATENT DOCUMENTS

| 4,383,985 | A | 5/1983 | Bartorelli et al. |
| 5,665,874 | A | 9/1997 | Kuhajda et al. |
| 6,235,967 | B1 | 5/2001 | Tan et al. |
| 6,251,384 | B1 | 6/2001 | Tan et al. |
| 6,716,627 | B2 | 4/2004 | Dobie et al. |
| 6,723,706 | B2 | 4/2004 | Uhlmann et al. |
| 2002/0090707 | A1 | 7/2002 | Enerback et al. |
| 2003/0005470 | A1 | 1/2003 | Sone et al. |
| 2004/0014051 | A1 | 1/2004 | Brown-Driver et al. |

FOREIGN PATENT DOCUMENTS

| WO | WO 98/54216 | 12/1998 |
| WO | WO 01/50653 | 7/2001 |
| WO | WO 03/064467 | 8/2003 |

OTHER PUBLICATIONS

Tockman et al (Cancer Res., 1992, 52:2711s-2718s).*
Stein et al (Cancer Research, Apr. 2004, 64:2805-2816).*
Freshney (Culture of Animal Cells, A Manual of Basic Technique, Alan R. Liss, Inc., 1983, New York, p. 4).*
Dermer (Bio/Technology, 1994, 12:320).*
Acevedo et al, "Metastatic Phenotype Correlates with High Expression of Membrane-Associated Complete B-Human Chorionic Gonadotropin In Vivo" American Cancer Society, vol. 78, 2388-2399, 1996.
Aslakson et al, "Selective Events in the Metastatic Process Defined by Analysis of the Sequential Dissemination of Subpopulations of a Mouse Mammary Tumor", Cancer Research, 52, 1399-1405, 1992.
Brooks et al, "Mutation of the *FOXC2* Gene in Familial Distichiasis", Journal of AAPOS, vol. 7 No. 5, 354-357, 2003.
Carlsson et al, "REVIEW Forkhead Transcripiton factors: Key Players in Development and Metabolism", Developmental Biology 250, 1-23, 2002.
Cederberg et al, "FOXC2 Is a Winged Helix Gene that counteracts Obesity, Hypertriglyceridemia, and Diet-Induced Insulin Resistance", Cell, vol. 106, 563-573, 2001.
Foulkes et al, "The Prognostic Implication of the Basal-Like (Cyclin Ehigh/p27low/p53+/ Glomeruloid-Microvascular-Proliferation+) Phenotype of BRCA1-Related Breast Cancer", Cancer Research 64, 830-835, 2004.
Hiemisch et al, "Expression of the mouse Fkh1/Mf1 and Mfh1 genes in late gestation embryos is restrictged to mesoderm derivatives", Mechanisms of Development, vol. 73, 129-132, 1998.
Kamei et al, "A forkhead transcription factor FKHR up-regulates lipoprotein lipase expression in skeletal muscle", FEBS Letters, 536, 232-236, 2003.
Kovacs et al, "Genetic Variation in the Human Winged Heliz/Forkhead Transcription Factor Gene FOXC2 in Pima Indians" Diabetes, vol. 52, 1292-1295, 2003.
Kume et al, "The murine winged helix transcription factors, Foxc1 and Foxc2, are both required for cardiovascular development and somitogenesis", Genes & Development 15: 2470-2482, 2001.
Miura et al, "Isolation of the Mouse (MFH-1) and Human (FKHL14) Mesenchyme Fork Head-1 Genes Reveals Conservation of Their Gene and Protein Structures", Genomics 41, 489-492, 1997.
Miura et al, "MFH-1, a new member of the fork head domain family, is expressed in developing mesenchyme", FEBS, vol. 326, No. 1,2, 3, 171-176, 1993.
Oft et al, "TGF-B1 and Ha-Ras collaborate in modulating the phenotypic plasticity and invasiveness of epithelial tumor cells", Genes & Development 10: 2462-2477, 1996.
Otsuka et al, "Differential Expression of the L-Plastin Gene in Human Colorectal Cancer Progression and Metastasis" Biochemical and Biphysical REsearch Communications, vol. 289, 876-881, 2001.
Seon et al, "Angiogenesis and Metastasis Marker of Human Tumors", Rinsho Byori 49: 1005-1013, 2001.
Sorlie et al, "Gene expression patterns of breast carcinomas distriguish tumor subclasses with clinical implications", PNAS, vol. 98, No. 19, 10869-10874, 2001.
Wang et al, "Loss of Heterozygosity and Its Correlation with Expression Profiles in Subclasses of Invasive Breat Cancers", Cancer Research 64, 64-71, 2004.
Wilm et al, "The forkhead genes, Foxc1 and Foxc2, regulate paraxial versus intermediate mesoderm cell fate", Developmental Biology, 271, 176-189, 2004.
Wucherpfening et al, "Structural Requirements for Binding of an Immunodominant Myelin Basic Protein Peptide to DR2 Isotypes and for Its Recognition by Human T Cell Clones", J. Exp. Med. vol. 179, 279-290, 1994.

(Continued)

*Primary Examiner* — Laura B Goddard
(74) *Attorney, Agent, or Firm* — Ropes & Gray LLP

(57) ABSTRACT

The invention relates to methods and compositions for inhibiting metastasis, such as by inhibiting FOXC2 expression or activity. The invention further relates to methods of prognosticating, diagnosing, and assisting in the diagnosis of metastasis in an individual, or of determining the metastatic potential of a tumor. The invention further relates to methods of identifying agents which inhibit metastasis.

5 Claims, 30 Drawing Sheets

OTHER PUBLICATIONS

Yanagisawa et al, "The FOXC2-512C>T varient is associated with hypertriglyceridaemia and increased serum C-peptide in Danish Caucasion glucose-tolerant sujbects", Diabetologia 46: 1576-1580, 2003.

Yang et al, "Twist, a Master Regulator of Morphogenesis, Plays an Essential Role in Tumor Metastasis", Cell, vol. 117, 927-939, 2004.

Zhong et al, "A Monoclonal Antibody That Induces Neuronal Apoptosis Binds a Metastasis Marker", Cancer Research 61, 5741-5748, 2001.

Tockman et al (Cancer Res. 1992, 52:2711s-2718s).

Busken, C et al, (Digestive Disease Week Abstracts and Itinerary Planner, 2003, abstract No. 850).

* cited by examiner

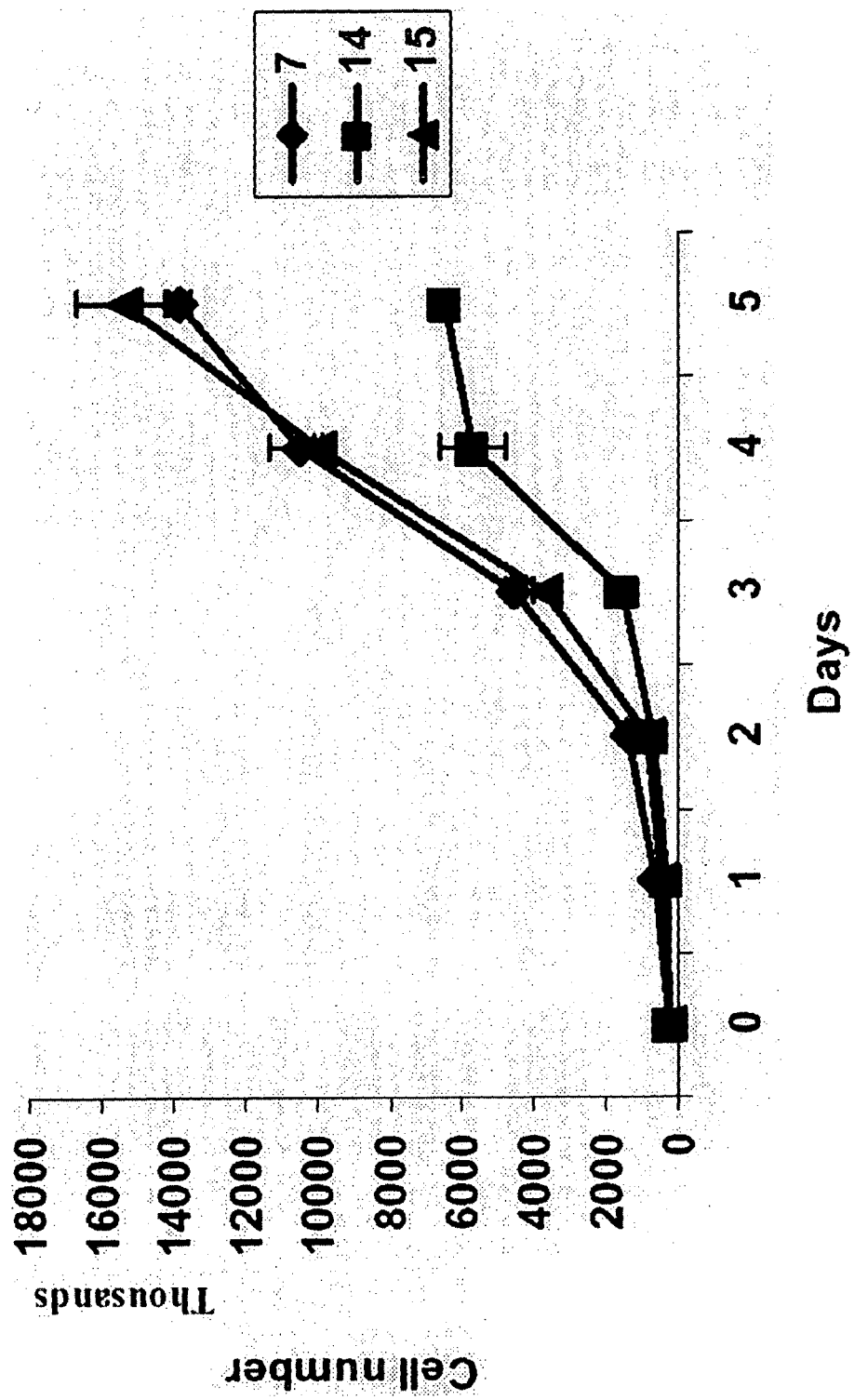

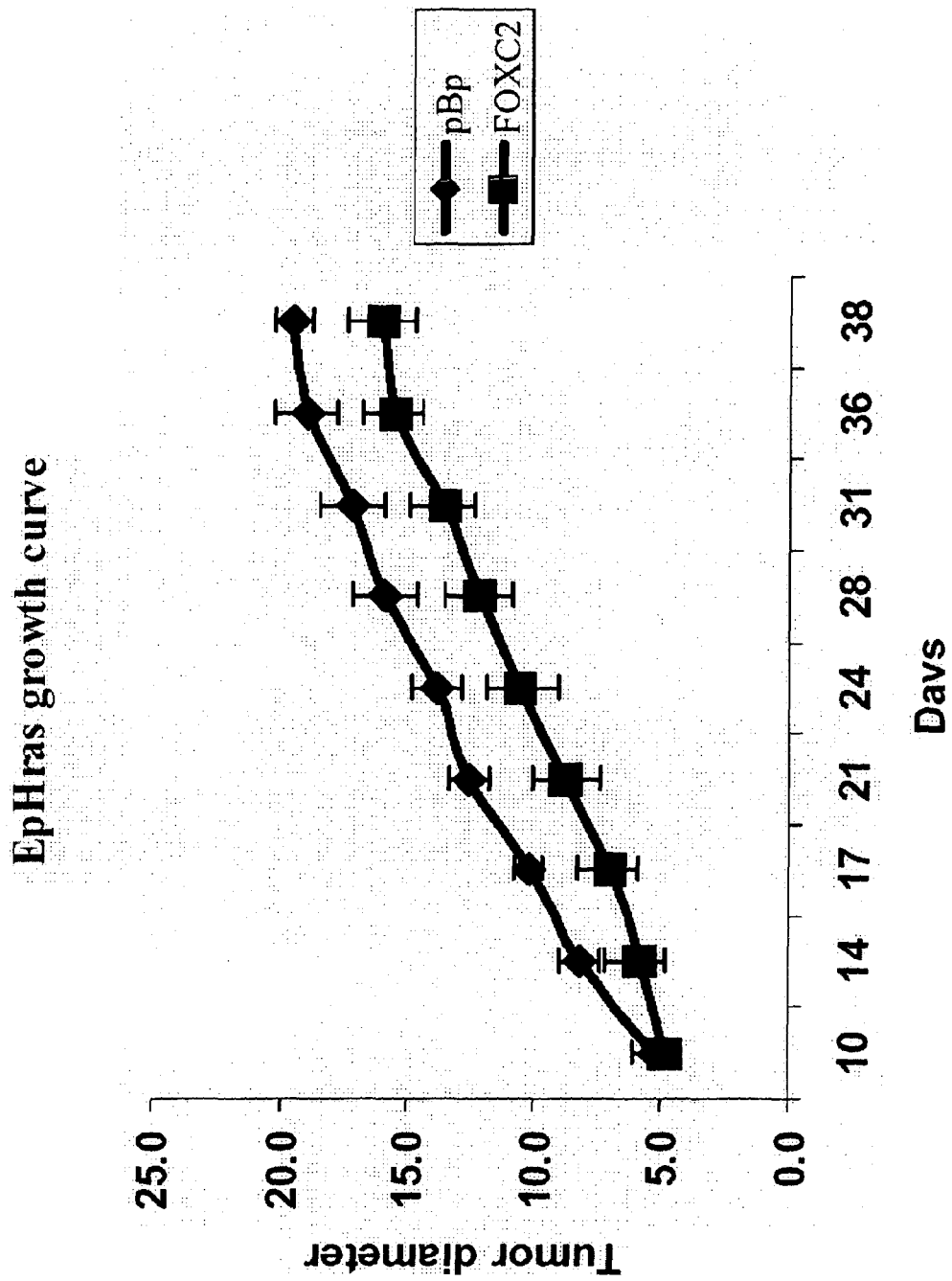

FOXC2

Vector

Correlation between FOXC2 staining and histological grade, ER-IHC and expression array tumor sub-types.

| Tumor type | High | Total | Percent High | p-Value |
|---|---|---|---|---|
| Grade I/II | 2 | 61 | 3.3 | 9.9E-01 |
| Grade III | 10 | 56 | 17.9 | 1.3E-03 |
| ER+ | 2 | 61 | 2.4 | 1.0E+00 |
| ER- | 10 | 34 | 29.4 | 3.2E-06 |
| Lum-ER+ | 1 | 65 | 1.5 | 1.0E+00 |
| HER2 | 3 | 34 | 8.8 | 4.8E-01 |
| Basal | 8 | 18 | 44.4 | 1.0E-06 |

USE OF FOXC2 IN DIAGNOSING, PREVENTING AND TREATING CANCER METASTASIS

CROSS-REFERENCE TO RELATED APPLICATIONS

This application is a continuation application of U.S. application Ser. No. 11/090,437, now abandoned, filed Mar. 25, 2005, entitled "METHODS OF DIAGNOSING, PREVENTING AND TREATING CANCER METASTASIS," which claims the benefit of the filing date of U.S. application Ser. No. 60/556,726, filed Mar. 26, 2004, entitled "METHODS OF DIAGNOSING, PREVENTING AND TREATING CANCER METASTASIS." The entire teachings of the referenced applications are incorporated by reference herein.

STATEMENT REGARDING FEDERALLY-SPONSORED RESEARCH OR DEVELOPMENT

The invention described herein was supported, in whole or in part, by Grant No. DAMD17-01-1-0457 from the Department of Defense, 1R21CA096689-01 From the National Cancer Institute and 1 F32 CA101507-01 from the National Institutes of Health. The United States government has certain rights in the invention.

BACKGROUND OF THE INVENTION

Cancer is considered to be a serious and pervasive disease. The National Cancer Institute has estimated that in the United States alone, 1 in 3 people will be struck with cancer during their lifetime. Moreover approximately 50% to 60% of people contracting cancer will eventually succumb to the disease. One particularly prevalent form of cancer, especially among women, is breast cancer. The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al, 1997, CA Cancer J. Clin. 47:5-27; Chu et al, 1996, J. Nat. Cancer Inst. 88:1571-1579). While the pathogenesis of breast cancer is unclear, transformation of normal breast epithelium to a malignant phenotype may be the result of genetic factors, especially in women under 30 (Miki et al., 1994, Science, 266:66-71). The discovery and characterization of BRCA1 and BRCA2 has expanded our knowledge of genetic factors that can contribute to familial breast cancer. Germ-line mutations within these two loci are associated with a 50 to 85% lifetime risk of breast and/or ovarian cancer (Casey, 1997, Curr. Opin. Oncol. 9:88-93; Marcus et al., 1996, Cancer 77:697-709). However, it is likely that other genetic and non-genetic factors also have a significant effect on the etiology of the disease.

Several general strategies have been developed to destroy cancer within the body. One method utilizes cytotoxic chemotherapeutics. These compounds are administered to cancer patients to preferentially destroy rapidly dividing malignant cells over normal, healthy cells. Examples of such compounds include 5-fluorouracil, cisplatin, and methotrexate. However, destruction of normal healthy cells by chemotherapeutics often leaves patients weakened and ill. Another approach involves reducing the supply of oxygen and nutrients to a tumor to prevent its growth by blocking the formation of new blood vessels, a process know as angiogenesis. Angiogenesis involves the formation of new blood vessels from existing blood vessels in response to various cell signals. Additional approaches include cancer vaccines and treatment of patients with antibodies directed to antigens that are overexpressed in cancer cells, such as the her2 receptor in breast cancer cells.

Another approach to treat cancer is to block the process of metastasis. Many tumors, such as breast tumors, can be either benign or malignant. Benign tumors are localized to one part of the body and do not spread to other parts of the body, and are not a threat to life. They can usually be removed, and in most cases, do not recur in patients. Malignant tumors, however, are cancerous and can invade and damage nearby tissues and organs, such as by entering the bloodstream or the lymphatic system, in a process known as metastasis. Thus, a benign breast tumor can metastasize into the liver or the lungs, resulting in death. Accordingly, anti-metastatic agents hold great promise in cancer treatment and in reducing mortality. In addition, such agents can also be used prophylactically after the removal of a precancerous tumor.

It would be advantageous to have new compositions and methods available for inhibiting tumor metastasis. It would also be advantageous to have new methods for identifying such compositions and methods. The present invention provides such compositions and methods.

SUMMARY OF THE INVENTION

The invention broadly relates to the treatment and diagnosis of cancer. Some aspects of the invention provide methods and composition for the treatment, prevention, diagnosis or prognosis of cancer metastasis. Other aspects relate to the identification of novel antitumor and antimetastatic agents.

One aspect of the invention provides compositions for inhibiting, preventing, aiding in the prevention, or decreasing the symptoms of tumor metastasis. One specific aspect of the invention provides a composition for use in inhibiting metastasis comprising: (a) a FOXC2 antagonist; and (b) a pharmaceutically suitable carrier. In one embodiment, the composition is a pharmaceutical compositions. In another embodiment, the composition further comprises an antineoplastic agent. In another embodiment, the FOXC2 antagonist is selected from the group consisting of an antibody, antibody fragment, an enzyme, a polypeptide and a nucleic acid. In one embodiment, the FOXC2 antagonist is an antibody or an antibody fragment that binds to a FOXC2 polypeptide. Antibodies include human and humanized antibodies. In some embodiments, the FOXC2 antagonist is present in, or conjugated onto, a liposome or microparticle that is of a suitable size for intravenous administration but that lodges in capillary beds.

The invention further provides methods of inhibiting, preventing, aiding in the prevention, or decreasing the symptoms associated with tumor/cancer metastasis. One specific embodiment provides a methods of inhibiting metastasis in an individual in need thereof, the method comprising administering to the individual an effective metastasis-inhibiting amount of a FOXC2 antagonist. The FOXC2 antagonist includes antibodies, antibody fragment, an enzyme, a polypeptide, nucleic acids and small molecules. Another embodiment further comprises administering the individual a therapeutically effective amount of an antineoplastic agent. Antineoplastic agents include, for example, cisplatin, carboplatin, oxaliplatin, radiation, CPT-11, paclitaxel, 5-flourouracil, leucovorin, epothilone, gemcitabine, UFT, herceptin, cytoxan, dacarbaxine, ifosfamide, mechlorethamine, melphalan, chlorambucil, anastrozole and exemstane, carmustine, lomustine, methotrexate, gemcitabine, cytarabine, fludarabine, bleomycin, dactinomycin, daunorubicin, doxorubicin, idarubicin, docetaxel, 5 vinblastine, vincristin, vinorelbine, topotecan, lupron, megace, leucovorin, Iressa, flavopiridol, immunomotherapeutic agents, ZD6474, SU6668, and valspodar.

The antagonist may be administered intravenously, intramuscularly, intradermally or subcutaneously, and may be adminstered systemically or at the site of a tumor. Individuals who may benefit from the therapeutic methods described herein include those having renal cell cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary carcinoma, mammary adenocarcinoma, pharyngeal squamous cell carcinoma, testicular cancer, gastrointestinal cancer, or stomach cancer. Other individuals include those with a ductal hyperplasia, a carcinoma in situ, an invasive ductal carcinoma, or a combination thereof. In one specific embodiment, the individual has breast cancer.

The invention further provides methods of identifying agents for the treatment of tumor metastasis. One such method comprises determining if the agent decreases the expression or activity of FOXC2 in a cell, wherein an agent that decreases the expression or activity of FOXC2 is a potential target for the treatment of tumor metastasis. In one embodiment, determining if the agent decreases the expression of FOXC2 in a cell comprises (a) contacting the cell with the agent; (b) determining a measure of FOXC2 expression; and (c) comparing the measure of FOXC2 expression to an appropriate control. In another embodiment, determining a measure of FOXC2 expression comprises determining FOXC2 mRNA levels or FOXC2 polypeptide levels. In another embodiment, determining a measure of FOXC2 expression comprises determining the activity of the FOXC2 promoter. In another embodiment, the cell comprises a recombinant nucleic acid comprising a FOXC2 promoter operably linked to a reporter gene. In another embodiment, an appropriate control comprises a measure of FOXC2 expression in a cell that is not contacted with the agent. In another embodiment, the method further comprises administering the agent to an animal having a tumor, and determining if the tumor metastasizes in the animal. In one embodiment, the animal is a mammal. In another embodiment, determining if the agent decreases the activity of FOXC2 in a cell comprises (a) contacting the cell with the agent; and (b) determining a measure of FOXC2 activity; and (c) comparing the measure of FOXC2 activity to an appropriate control. In another embodiment, a measure of FOXC2 activity comprises FOXC2 transcriptional activating activity. In another embodiment, determining a measure of FOXC2 activity comprises determining the expression level of a gene whose transcription is regulated by FOXC2. In another embodiment, the cell comprises a recombinant nucleic acid comprising a promoter and a reporter gene operably linked to the promoter, wherein the promoter is transcriptionally regulated by FOXC2. In one embodiment, the methods for identifying therapeutic agents further comprise administering the agent to a mammal having a tumor, and determining if the tumor metastasizes.

Another aspect of the invention provides diagnostic methods for tumor metastasis. One specific aspect of the invention provides a method for predicting the likelihood that the tumor in an individual will metastasize, the method comprising (a) determining the level of a FOXC2 gene product in a biological sample obtained from the tumor of the individual; and (b) comparing the level with a control level, wherein if the level determined in (a) is greater than the control level, the individual is said to have increased likelihood of the tumor metastasizing.

Another aspect of the invention provides a method of predicting the likelihood of development of a tumor metastasis in an individual, comprising the steps of: (a) obtaining a biological sample from the individual to be tested; (b) determining the level of a FOXC2 gene product in the biological sample; and (c) comparing the level determined in (b) with an appropriate control, wherein if the level determined in (b) is greater than the level of the FOXC2 gene product in said control sample, then the individual has an increased likelihood of developing a metastatic condition. In one embodiment, the biological sample comprises tumor tissue. In one embodiment, the FOXC2 gene product is a FOXC2 polypeptide or a FOXC2 mRNA. In another embodiment, determining the level of the FOXC2 gene product in the biological sample comprises determining the bioactivity of a FOXC2 polypeptide in the sample. In another embodiment, the method further comprises determining the level of at least one additional gene product in the sample that is indicative of metastasis.

Another aspect of the invention provides a method of predicting the likelihood of development of a metastatic condition in an individual, comprising the steps of: (a) obtaining a nucleic acid sample from the individual; and (b) determining if the nucleic sample contains at least one mutation in the FOXC2 gene which results in increase FOXC2 expression or activity, wherein the presence of at least one said mutation indicates that the individual is at risk of developing cancer metastasis. In another embodiment, determining if the nucleic sample contains mutations in the FOXC2 comprising determining the nucleotide sequence of at least part of the FOXC2 gene, such as part of the FOXC2 coding sequence or intro-exonboundaries.

The invention further provides agents for the manufacture of medicaments to treat any of the disorders described herein. Any methods disclosed herein for treating, preventing or aiding in the prevention of a disorder, such as of cancer metastasis, by administering an agent to an individual may be applied to the use of the agent in the manufacture of a medicament to treat that disorder. For example, in one specific embodiment, a FOXC2 antagonist, such as an hairpin or double-stranded antisense nucleic acid which targets FOXC2 mRNA or a monoclonal human antibody specific for a FOXC2 polypeptide, is used in the manufacture of a medicament for the treatment or prevention of cancer metastasis.

BRIEF DESCRIPTION OF THE DRAWINGS

FIG. 1B: Metastatic properties of mouse mammary carcinoma cells used for microarray analysis is represented graphically. FIG. 1B: FOXC2 is specifically expressed in highly metastatic 4T1 cells, the Average value of FOXC2 expression in four primary tumors formed by each cell line, measured by microarray analysis is represented and each bar represents the mean±SEM (Standard error of the mean). FIG. 1C: FOXC2 expression data from the microarray is validated using realtime PCR using RNA isolated from the tumors formed by these four cell lines and compared the expression to the 67NR cells, GAPDH is used to normalize the data. FIG. 1D: FOXC2 protein is expressed only in 4T1 cells, □-actin is used as a loading control. FIG. 1E: FOXC2 is expressed in 5 out of six metastatic cells compared to 1 out of five non metastatic cells evidenced by immunoblotting, b-actin is used as a control.

Figure 2A:
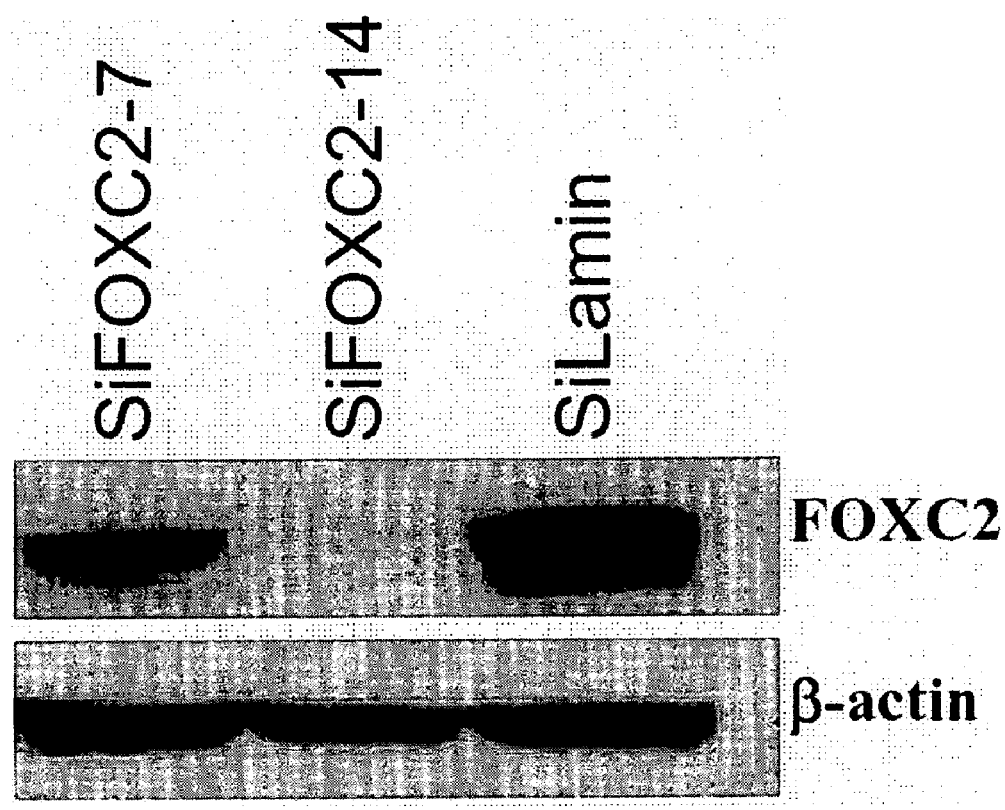
Figure 2C:
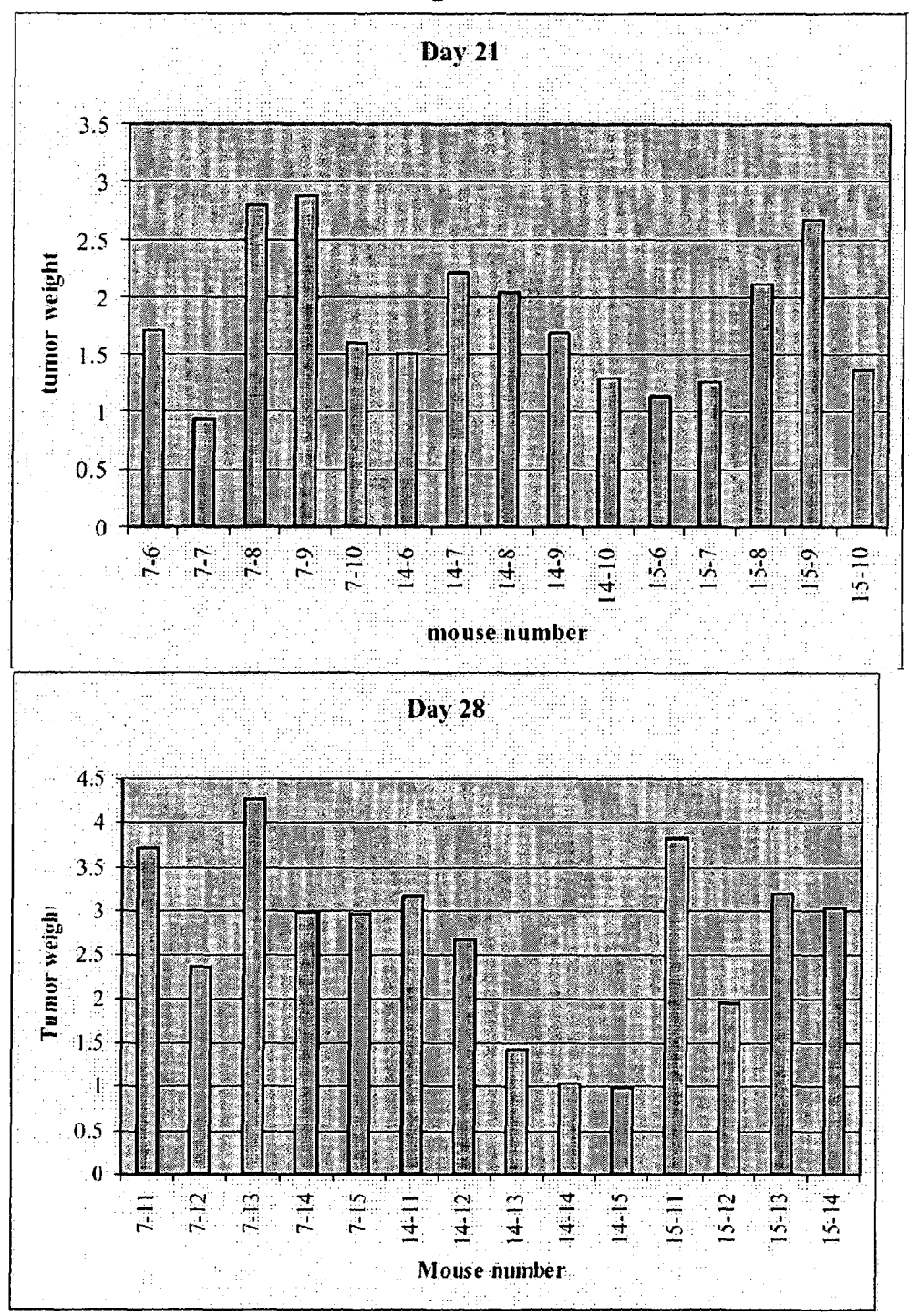
Figure 2D:
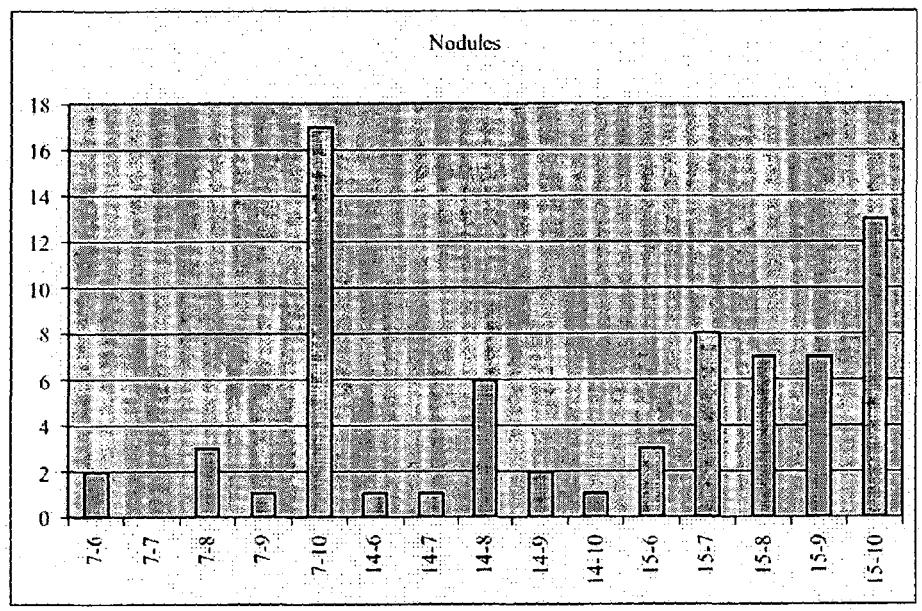
Figure 2D:
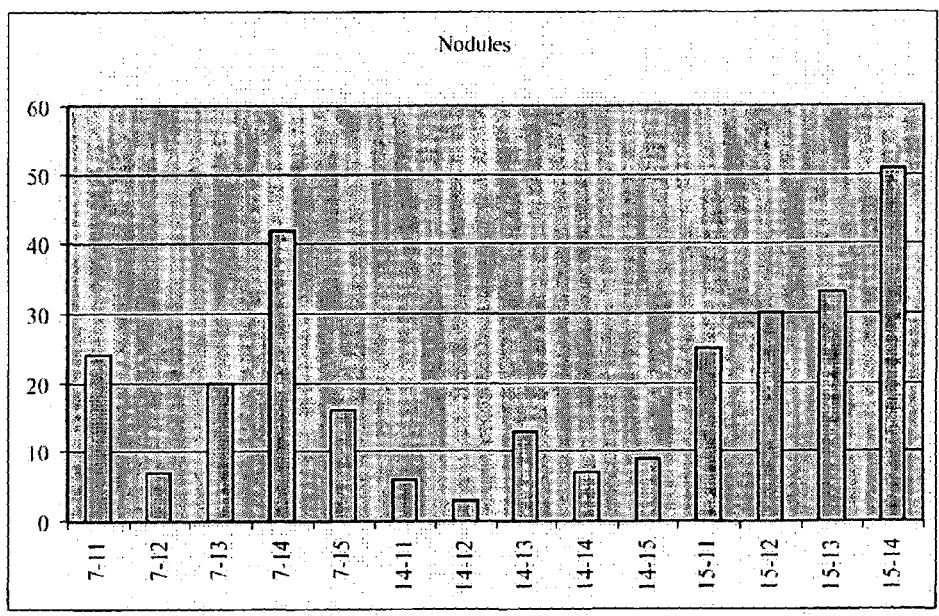
Figure 2E:
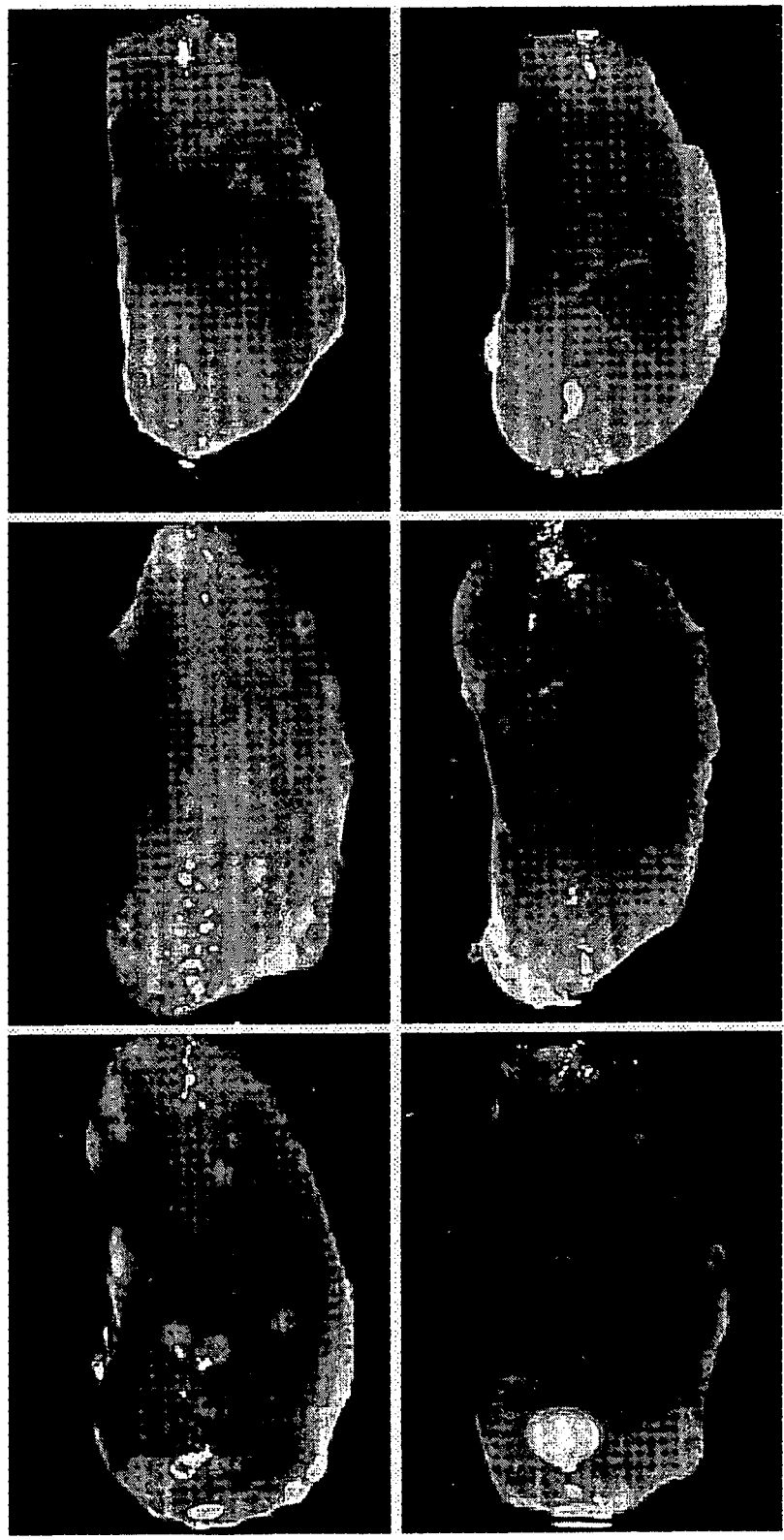

FIGS. 2A-2E show that FOXC2 is necessary for metastasis in 4T1 cells. FIG. 2A: Short hairpin oligos against FOXC2 suppress the expression of FOXC2 either completely (Si-FOXC2-14) or partially (SiFOXC2-7) compared to the control (Si-Lamin) oligos FIG. 2B: In vitro, 4T1 cells with SiFOXC2-14 grow slower than Si-Lamin and SiFOXC2-7. FIG. 2C: In vivo, there is a marginal difference in tumor growth by 4T1 SiFOXC2-14 cells compared to the Si-FOXC2-7 and Si-Lamin. FIG. 2D: Lungs of the mice with 4T1 cells expressing Si-FOXC2-14 and SiFOXC2-7 oligos had reduced number of nodules compared to the control Si-Lamin oligo. FIG. 2E: The data is represented graphically.

Figure 3A:
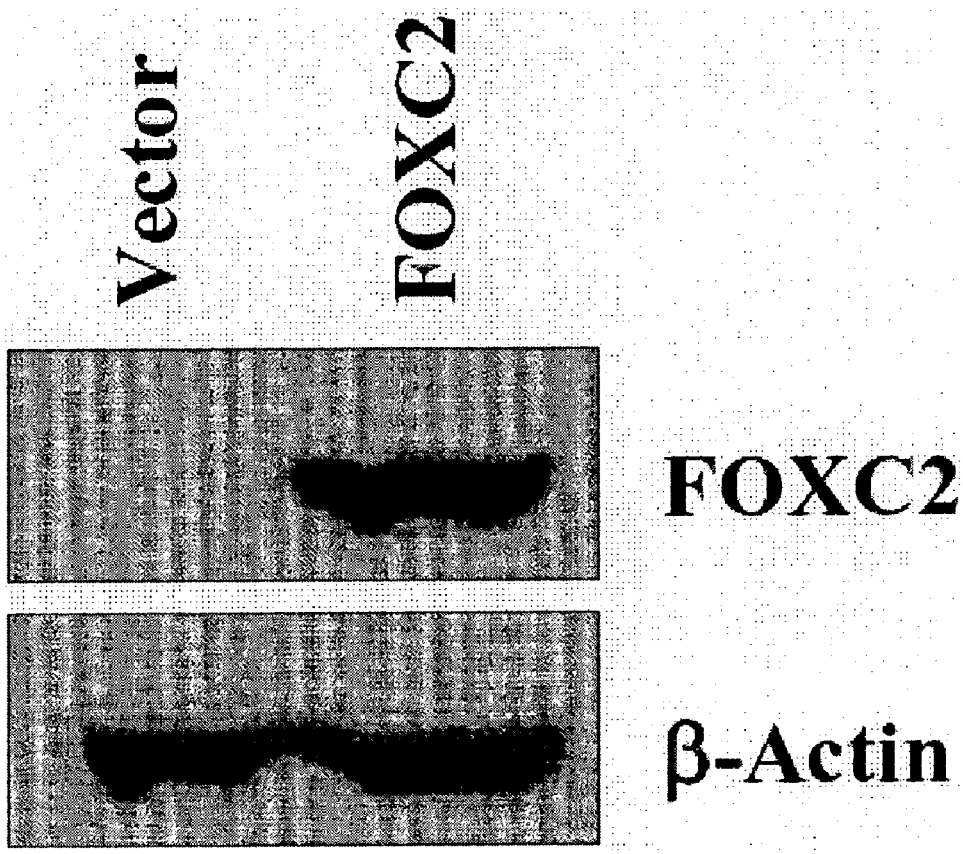
Figure 3D:
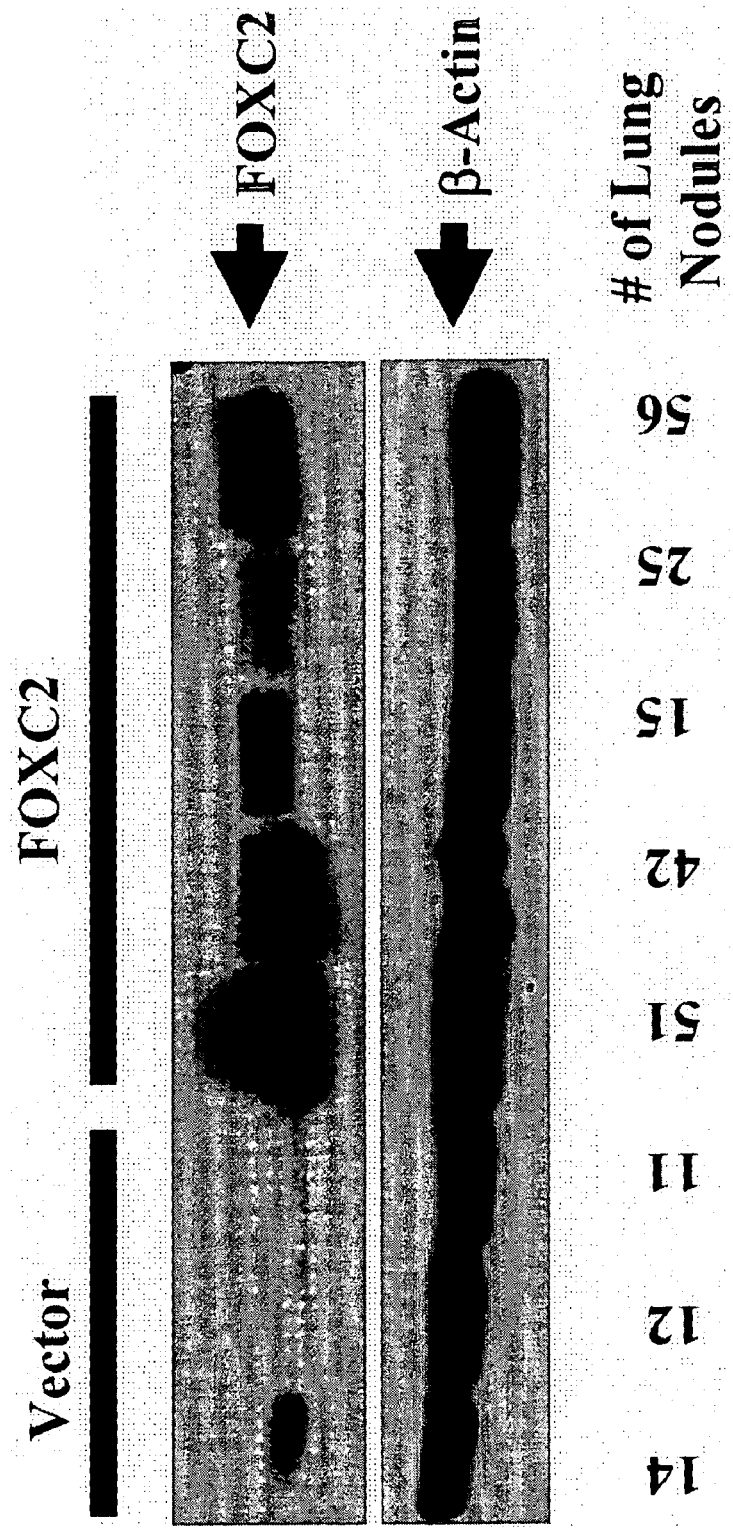

FIGS. 3A-3D show that FOXC2 is sufficient to promote metastasis in non-metastatic EpRas mouse mammary carcinoma cells. FIG. 3A: FOXC2 protein was overexpressed in EpRas cells using retrovirus and analyzed by imunoblotting, $\beta$-actin is used as a loading control. FIG. 3B: EpRas cells expressing FOXC2 grow similar to the control cells in the subcutaneous site of nude mice. Each data point represents the mean diameter±SEM of 10 primary tumors. FIG. 3C. EpRas cells expressing FOXC2 produced 32±6.4 (SEM) nodules compared to 11.6±0.6 (SEM) nodules vector infected cells. FIG. 3D. Level of FOXC2 expression in the primary tumor formed by EpRas cells expressing either vector or FOXC2 correspond to the number of nodules assessed by FOXC2 immunoblot and counting the visible nodules in the lungs of corresponding mouse. $\beta$-actin is used as a loading control.

Figure 4A:
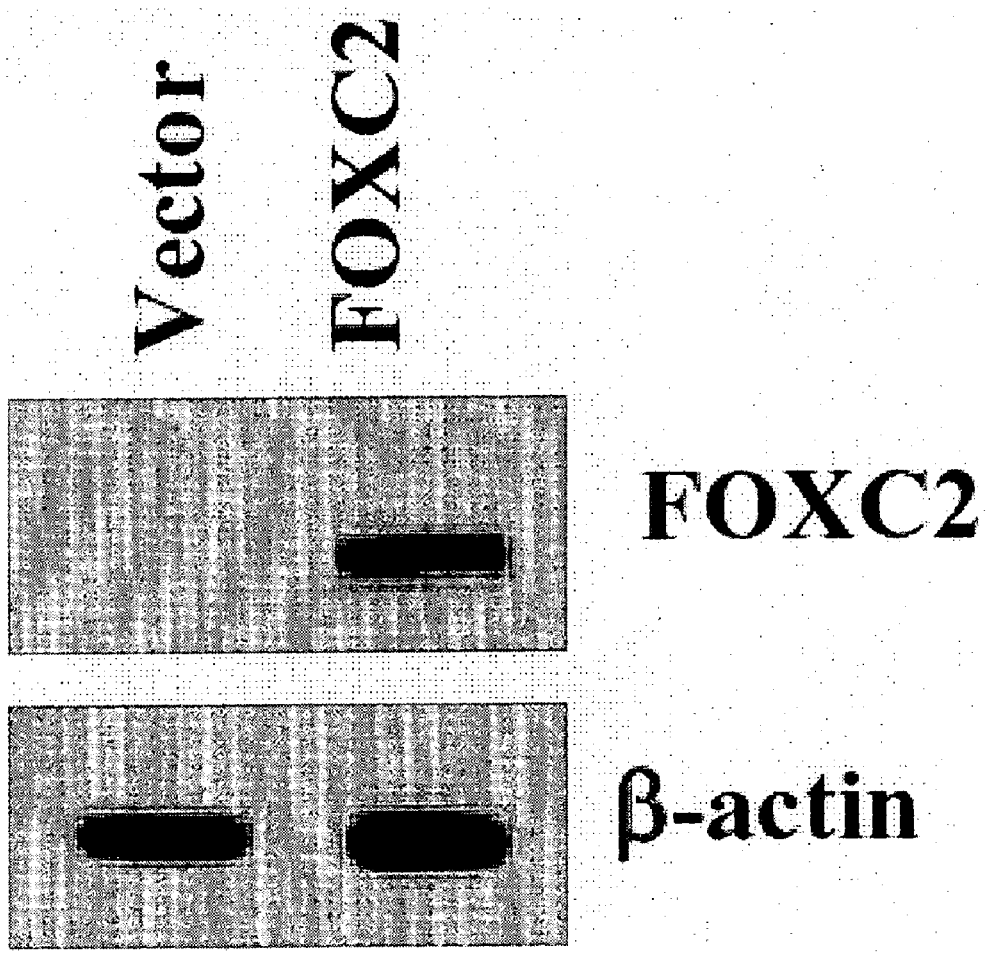
Figure 4B:
Figure 4B:
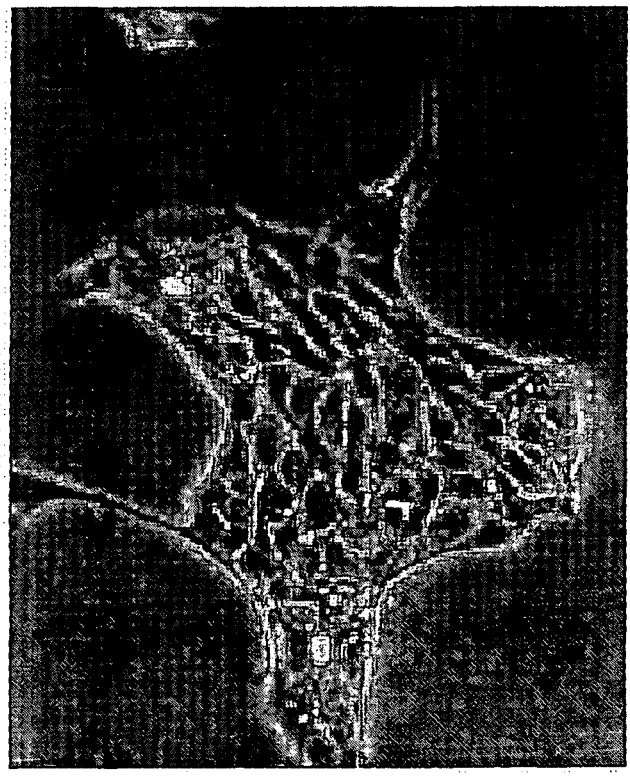
Figure 4C:
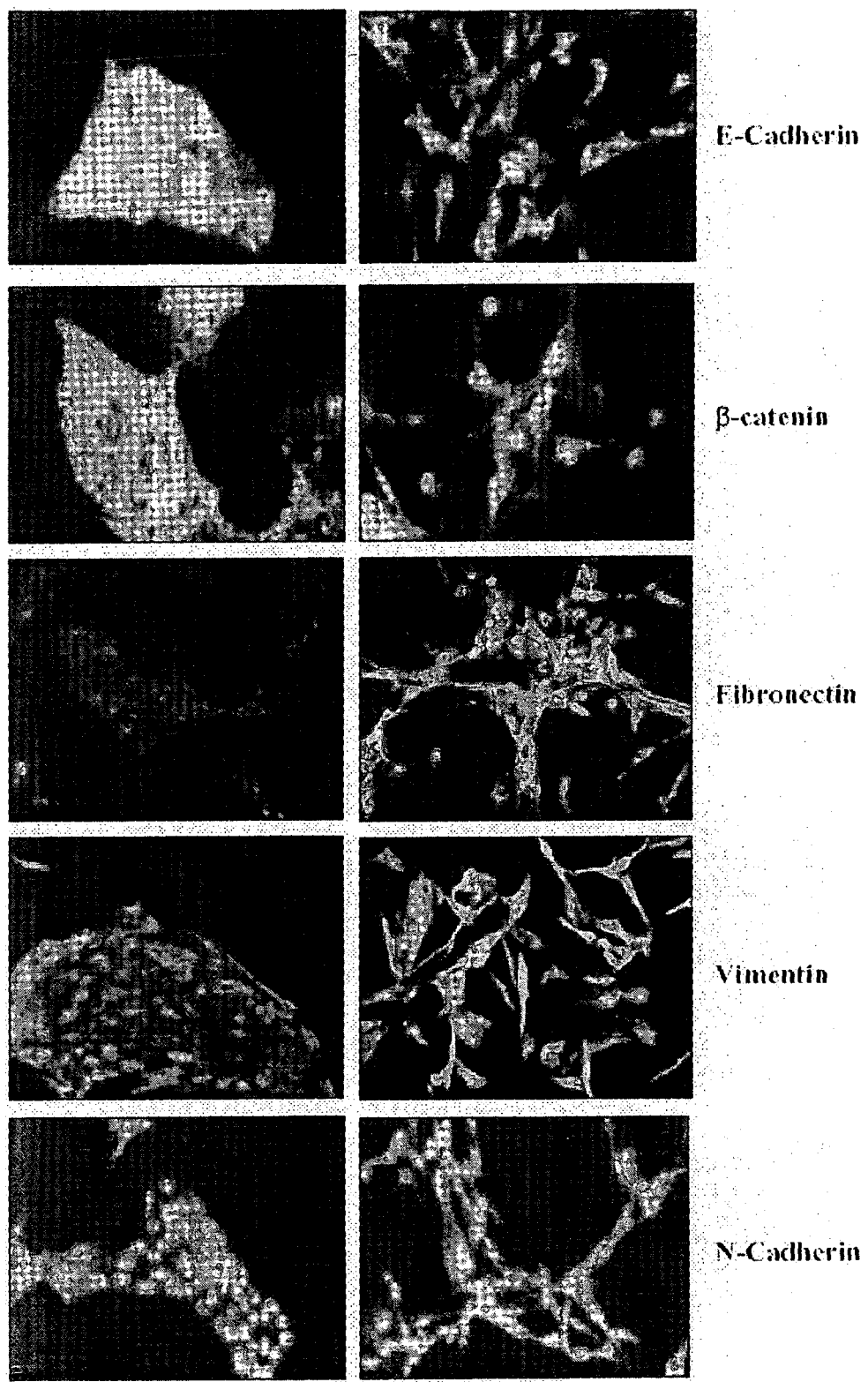
Figure 4D:
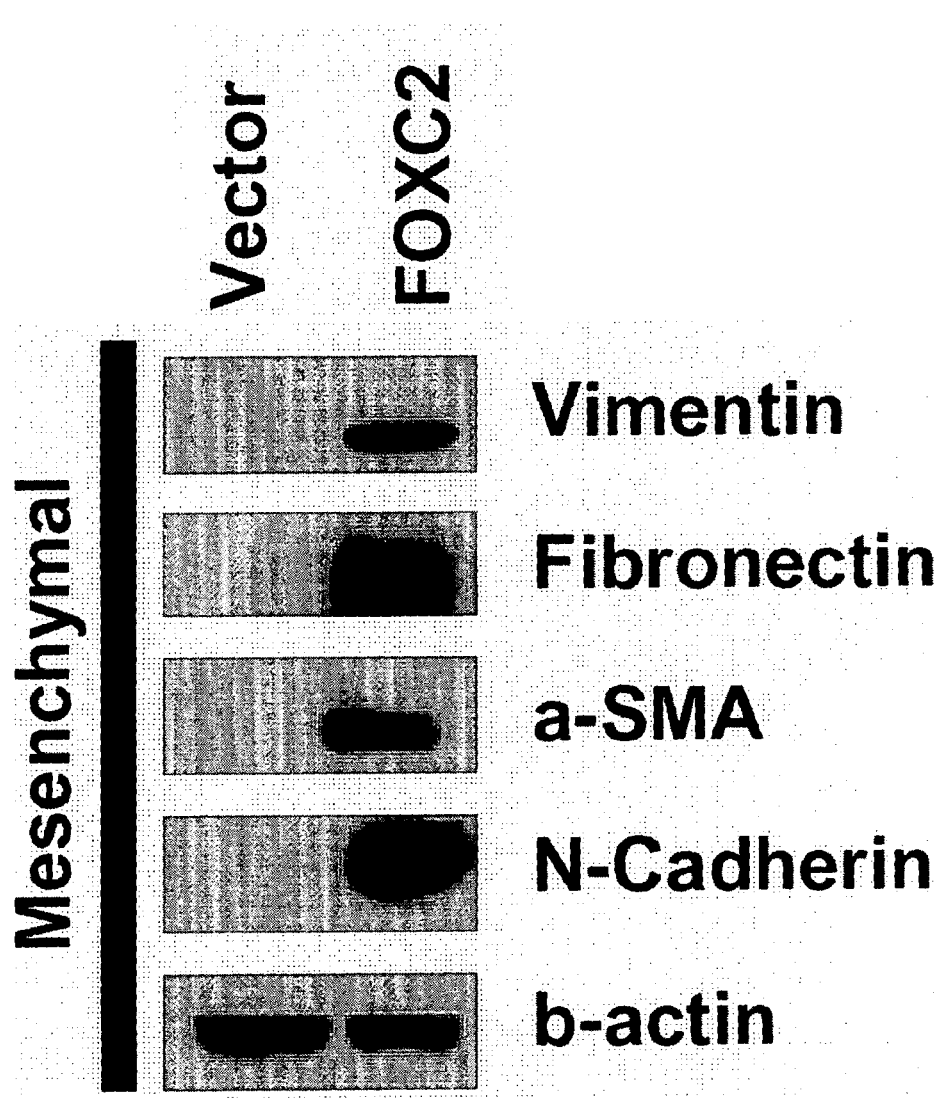
Figure 4E:
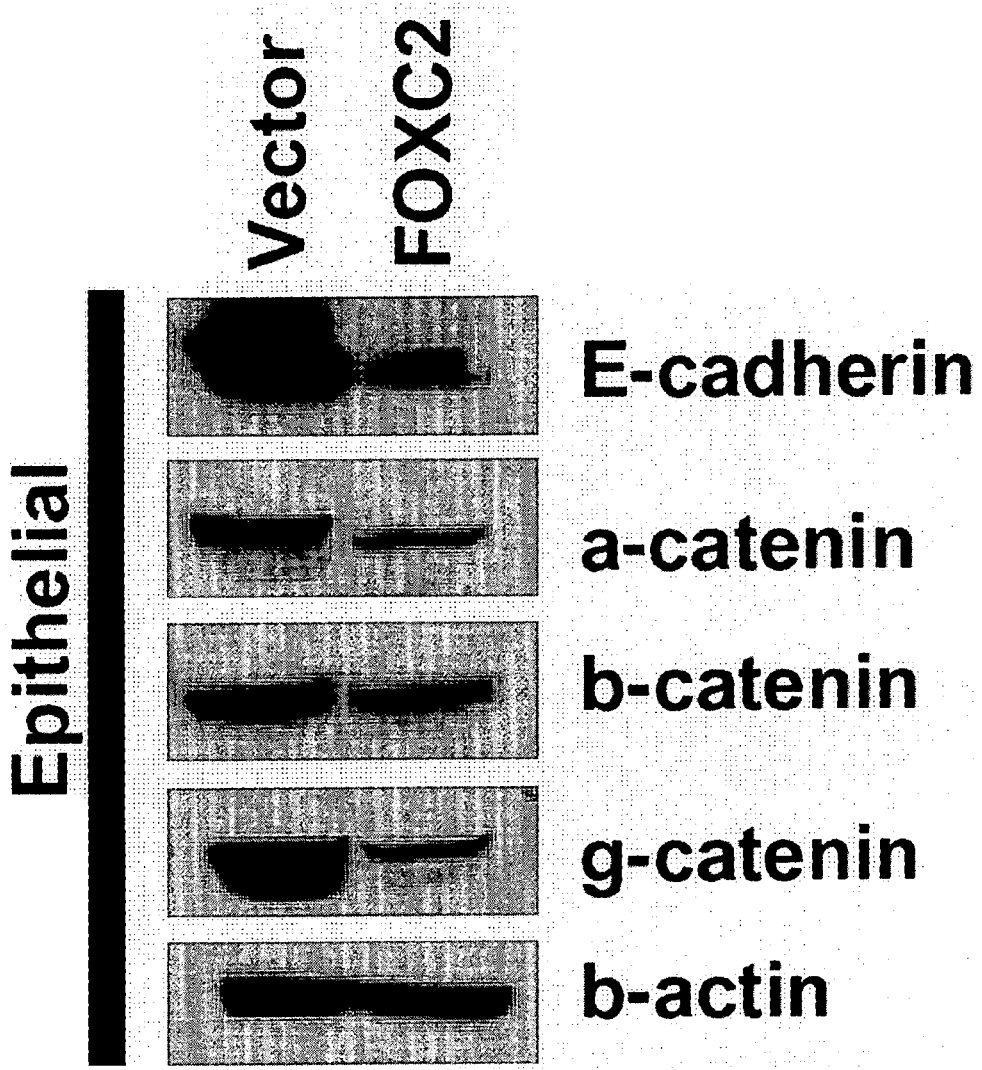
Figure 4F:
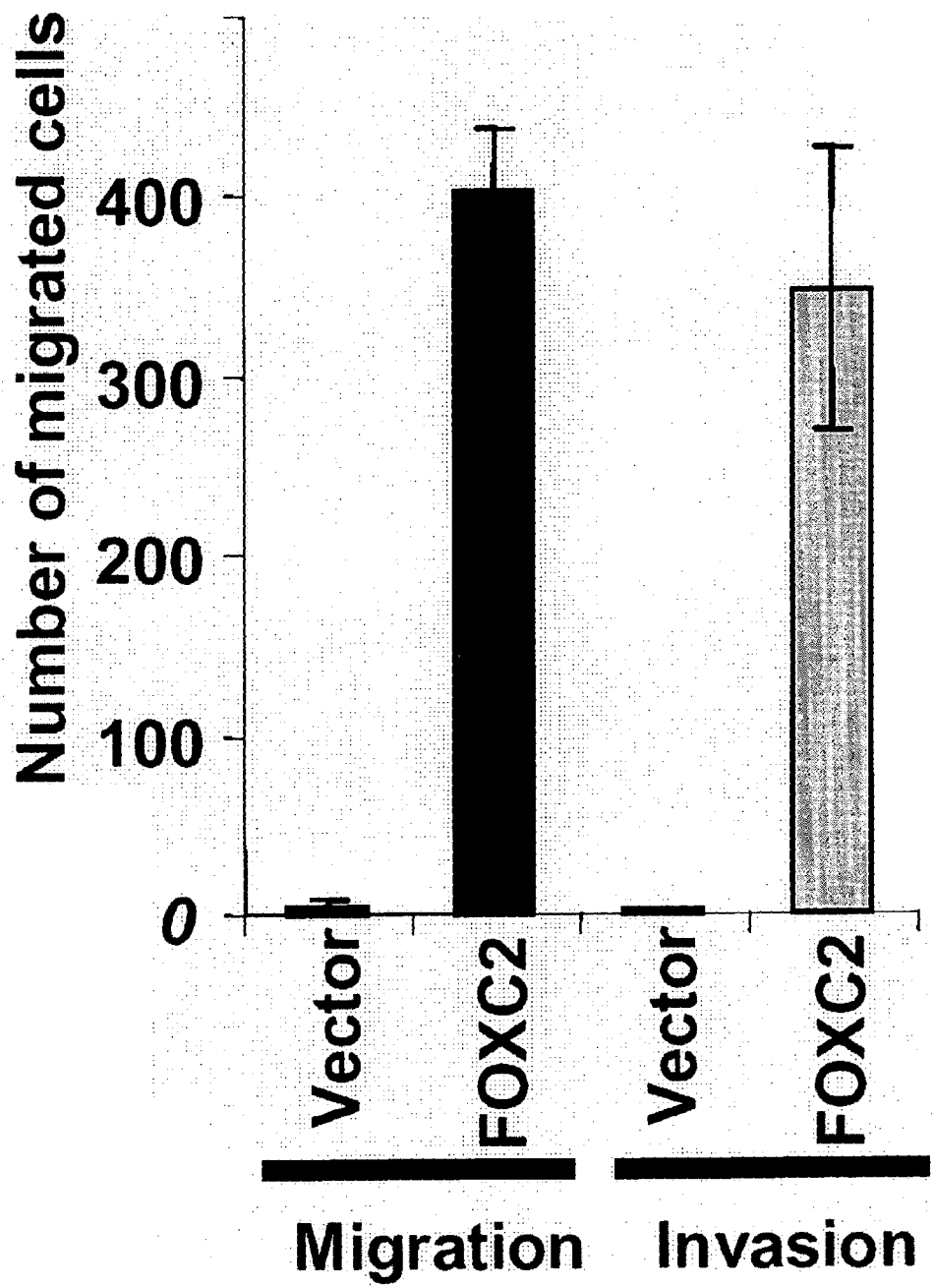
Figure 4G:
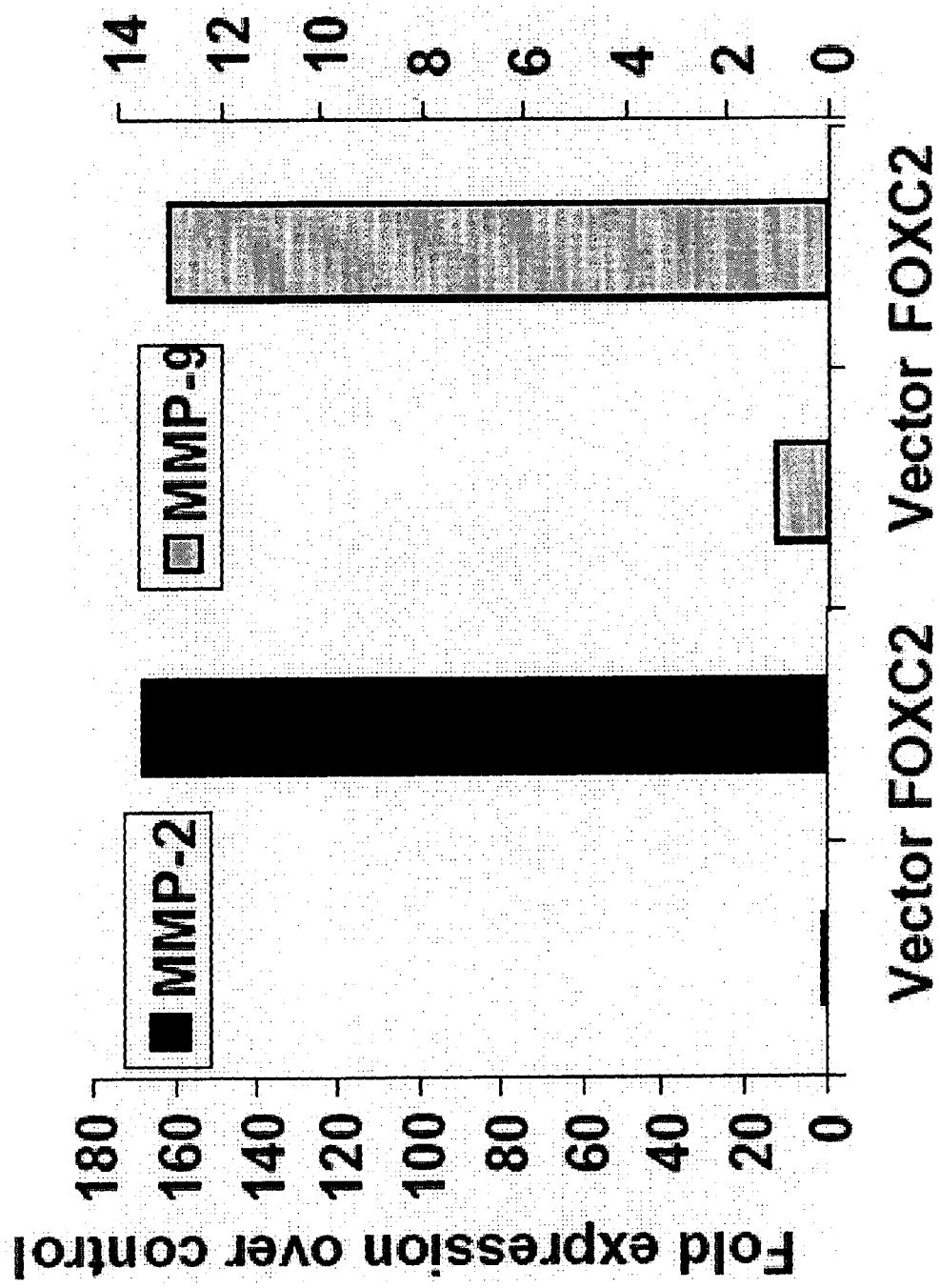
Figure 4H:
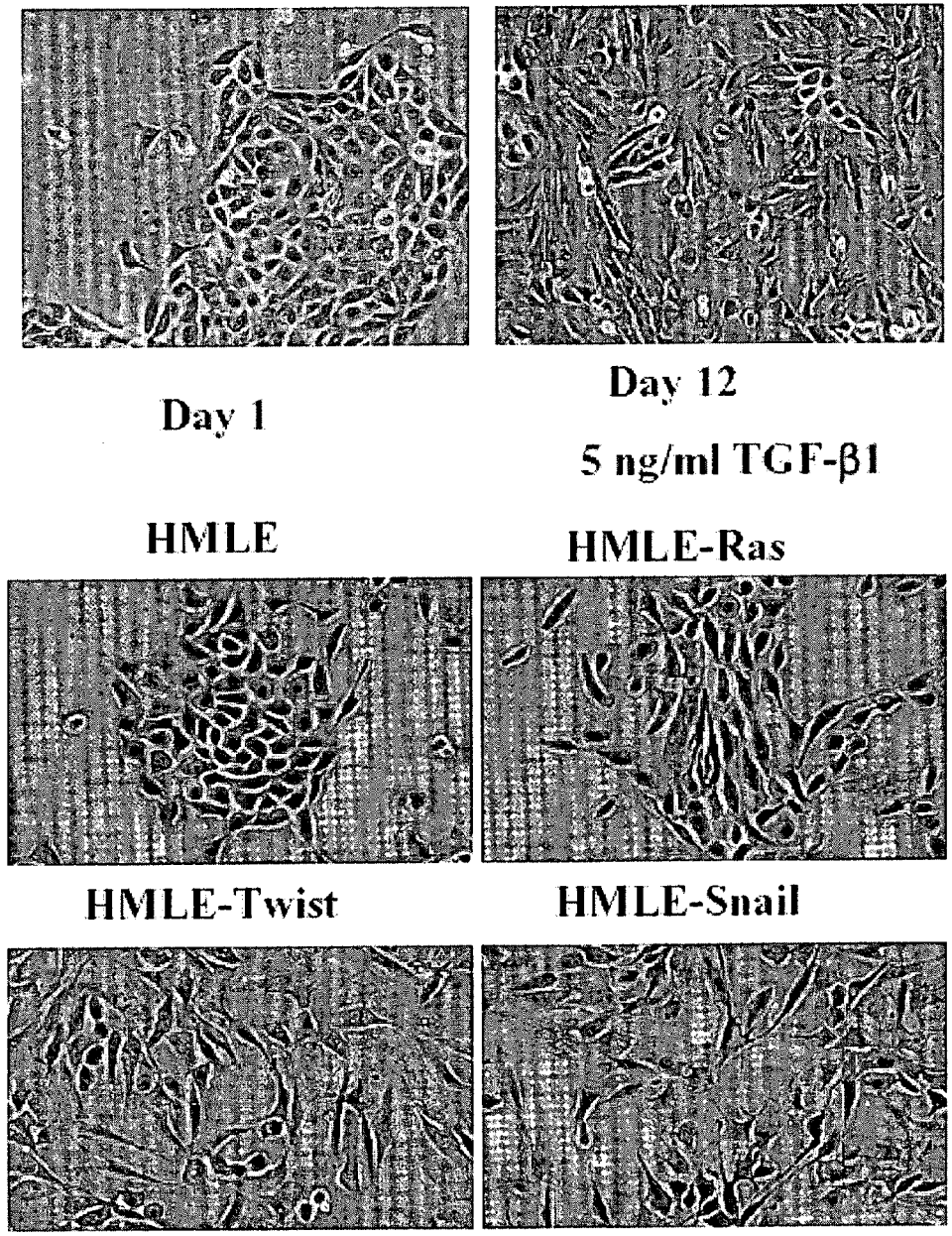
Figure 4I:
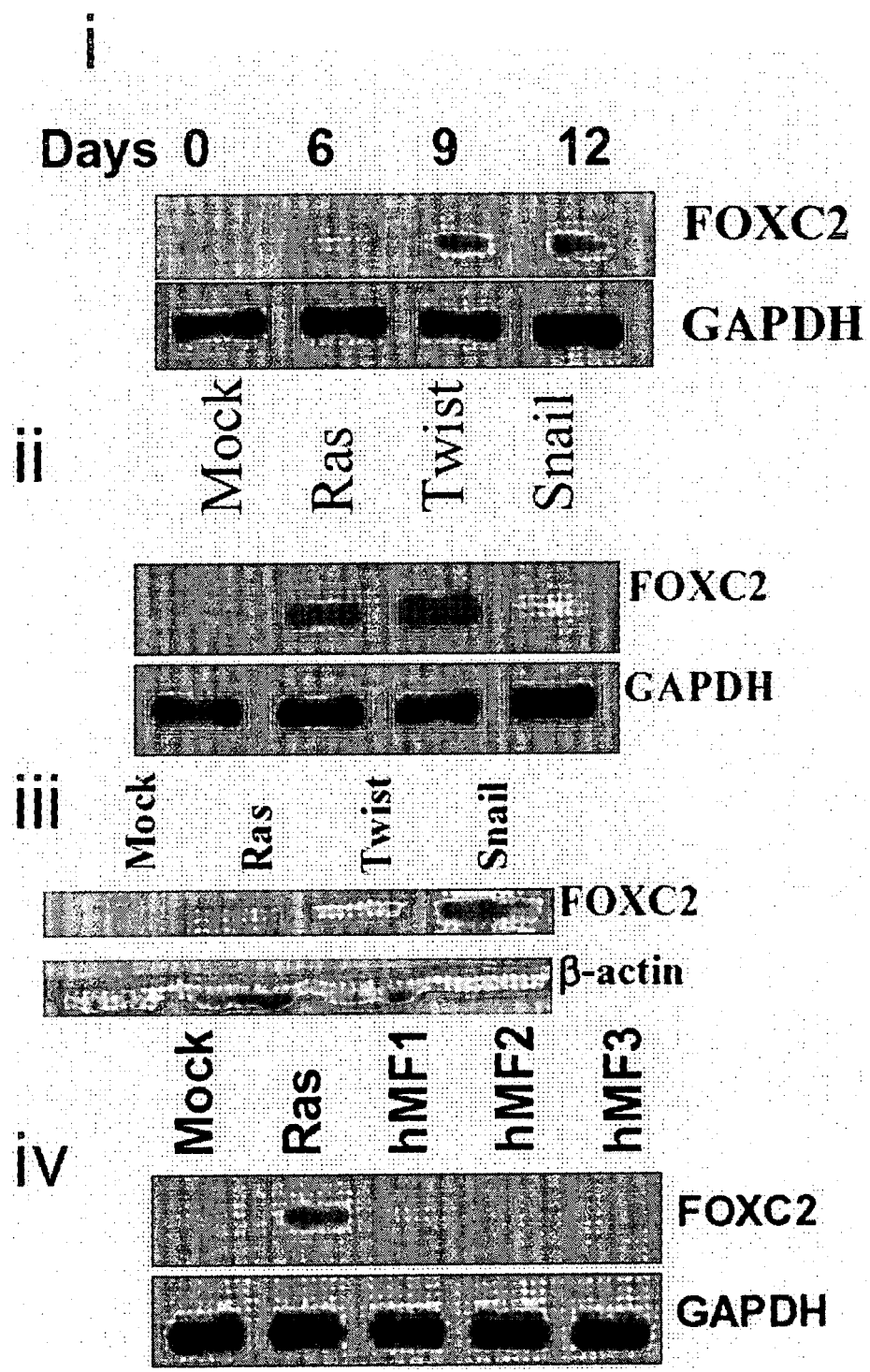

FIGS. 4A-4J show that FOXC2 induces EMT in MDCK cells. FIG. 4A. FOXC2 protein was overexpressed using retrovirus in MDCK cells and examined by immunoblotting, $\beta$-actin is used as a loading control. FIG. 4B: Overexpression of FOXC2 in MDCK cells induces morphological changes similar to EMT revealed by phase contrast microscopy. FIG. 4C. Overexpression of FOXC2 leads to partial downregulation epithelial marker E-Cadherin and no change in $\beta$-catenin compared to induction of mesenchymal markers such as fibronectin and vimentin evidenced by immunoflourescence. The green signal represents the staining of corresponding protein, and the blue signal represents the nuclear DNA staining by Hoechst. FIGS. 4D-4E: FOXC2 expression partially downregulates epithelial markers and induce the expression of mesenchymal markers evidenced by immunoblot analysis, $\beta$-actin is used as a loading control. FIG. 4F: FOXC2 promotes migration and invasion of MDCK cells assessed by Boydon-chamber assay. The migration and invasion ability is presented as total number of cells migrated to the bottom chamber. Each bar represents the mean±SEM of samples measured in triplicate and each experiment is repeated at least three times. FIG. 4G: FOXC2 induce the expression of MMP2 and MMP9 to facilitate migration and invasion measured by ELISA; the data represents the fold expression in FOXC2 expressing cells compared to the vector infected control cells. Each bar is the average of triplicates and each experiment repeated twice. FIG. 4H: FOXC2 expression is induced when HMLE cells underwent EMT by treatment with TGF-b 1 or increased expression of genes capable of inducing EMT such as Ras, Twist and Snai 1 by RT-PCR GAPDH is used as a loading control. FIG. 4I: FOXC2 induces the expression of TGF-$\beta$1 measured by ELISA; the data represents the fold expression in FOXC2 expressing cells compared to the vector infected control cells. Each bar is the average of triplicates and each experiment repeated twice.

Figure 5A:
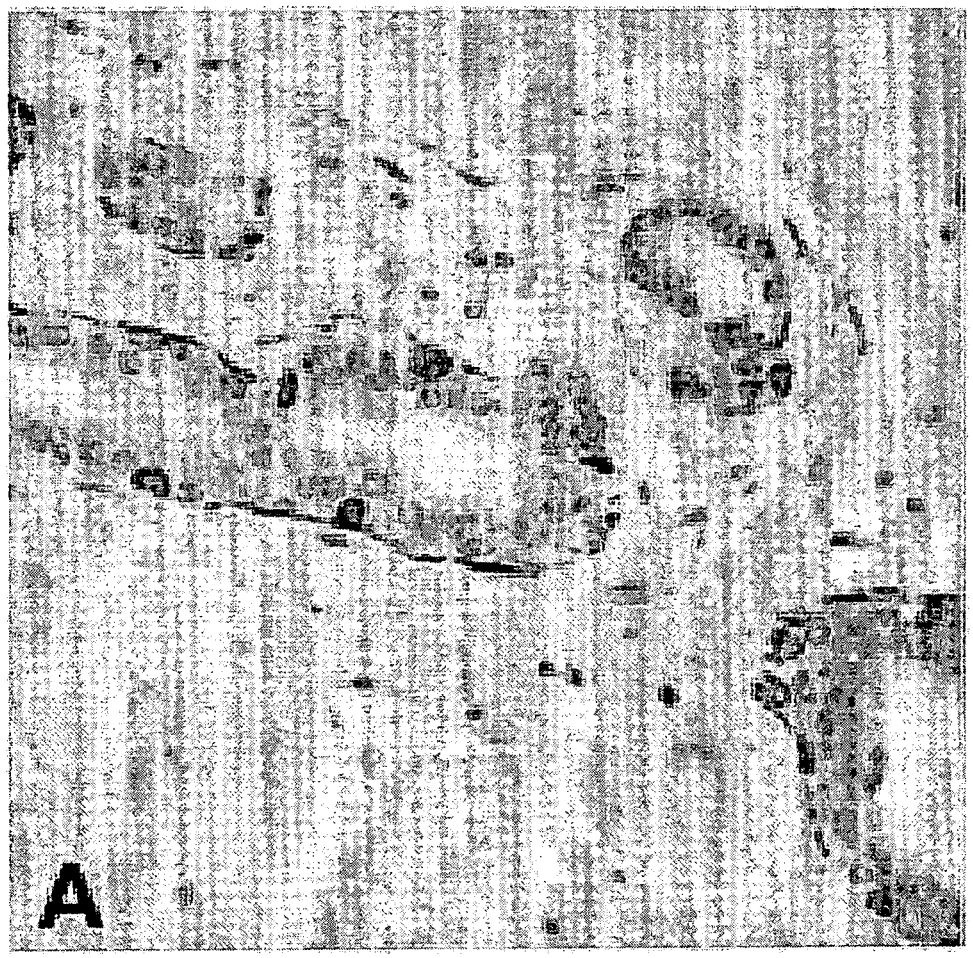
Figure 5B:
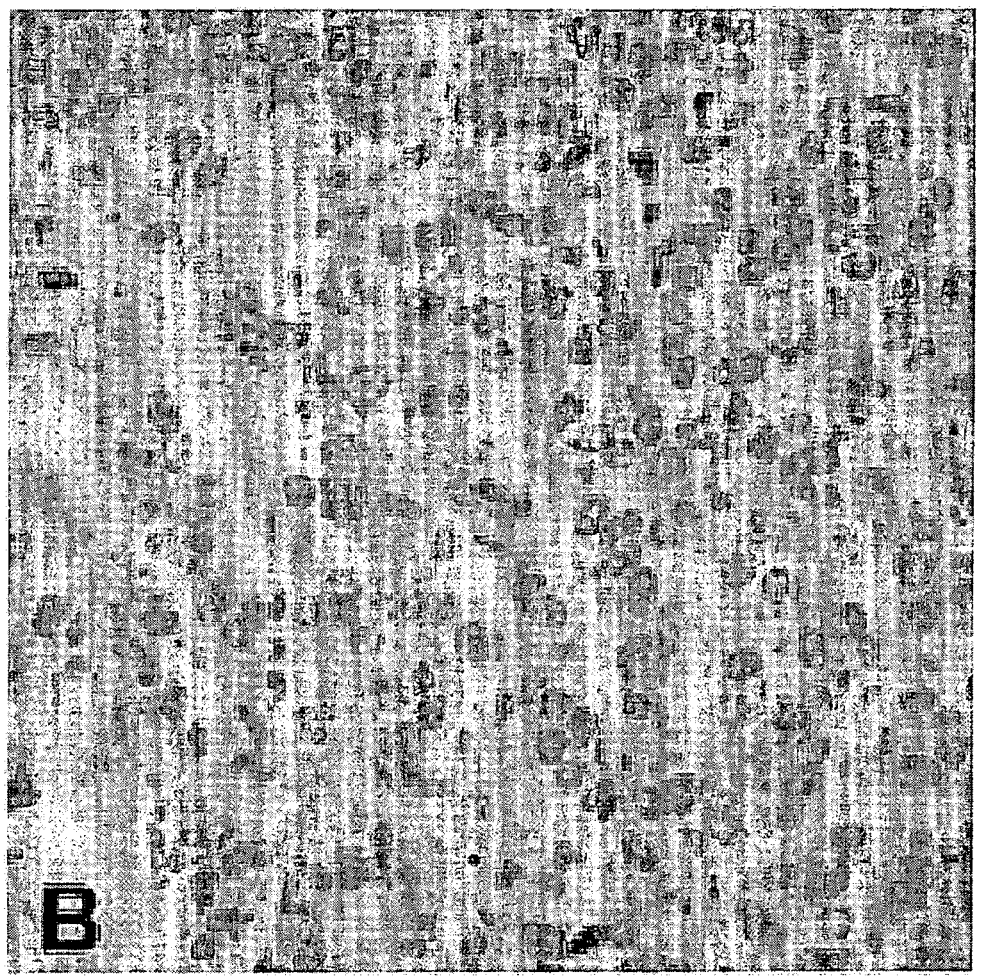
Figure 5C:
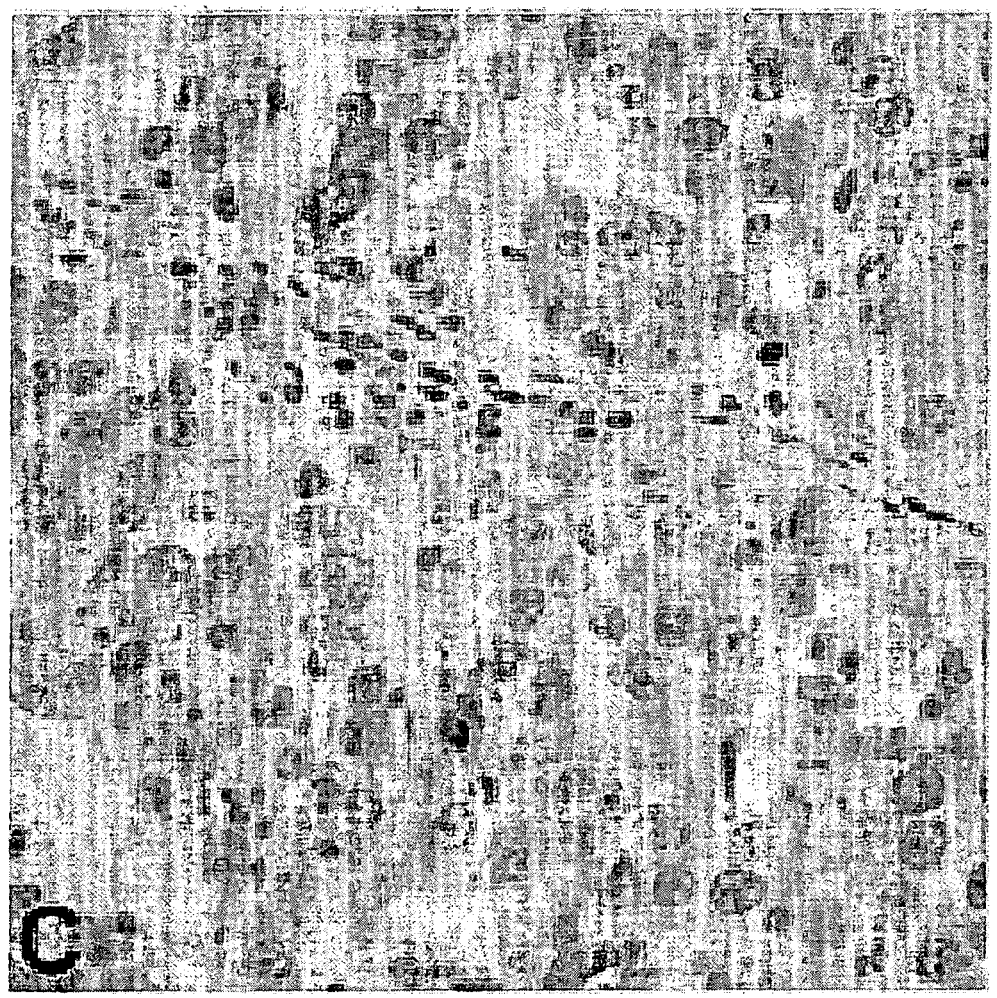
Figure 5D:
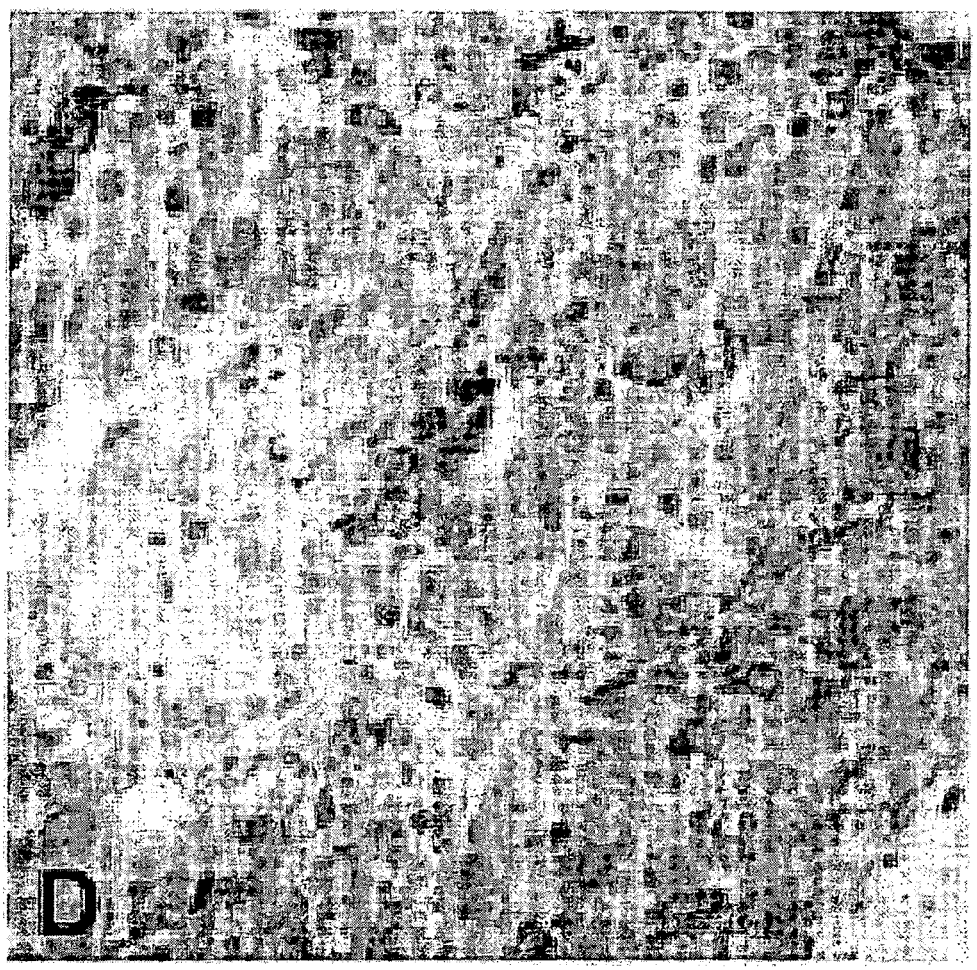
Figure 5E:
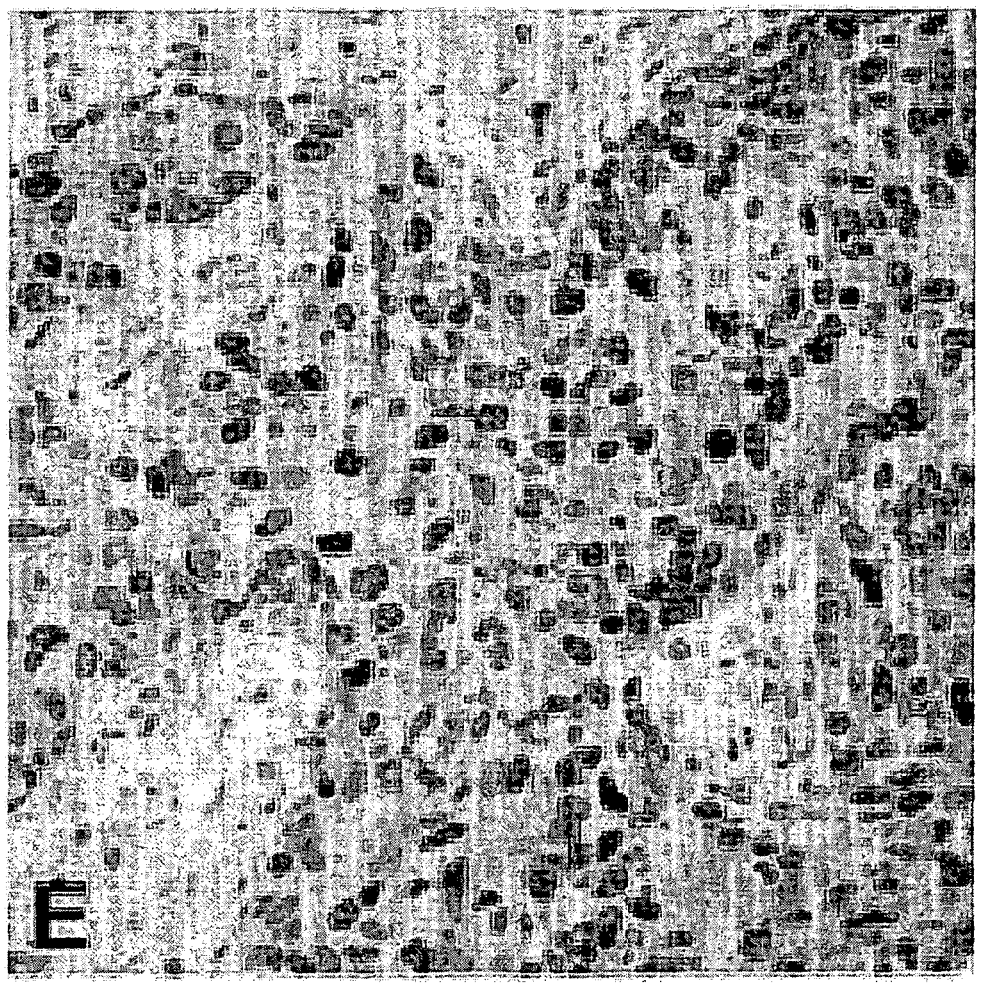
Figure 5F:
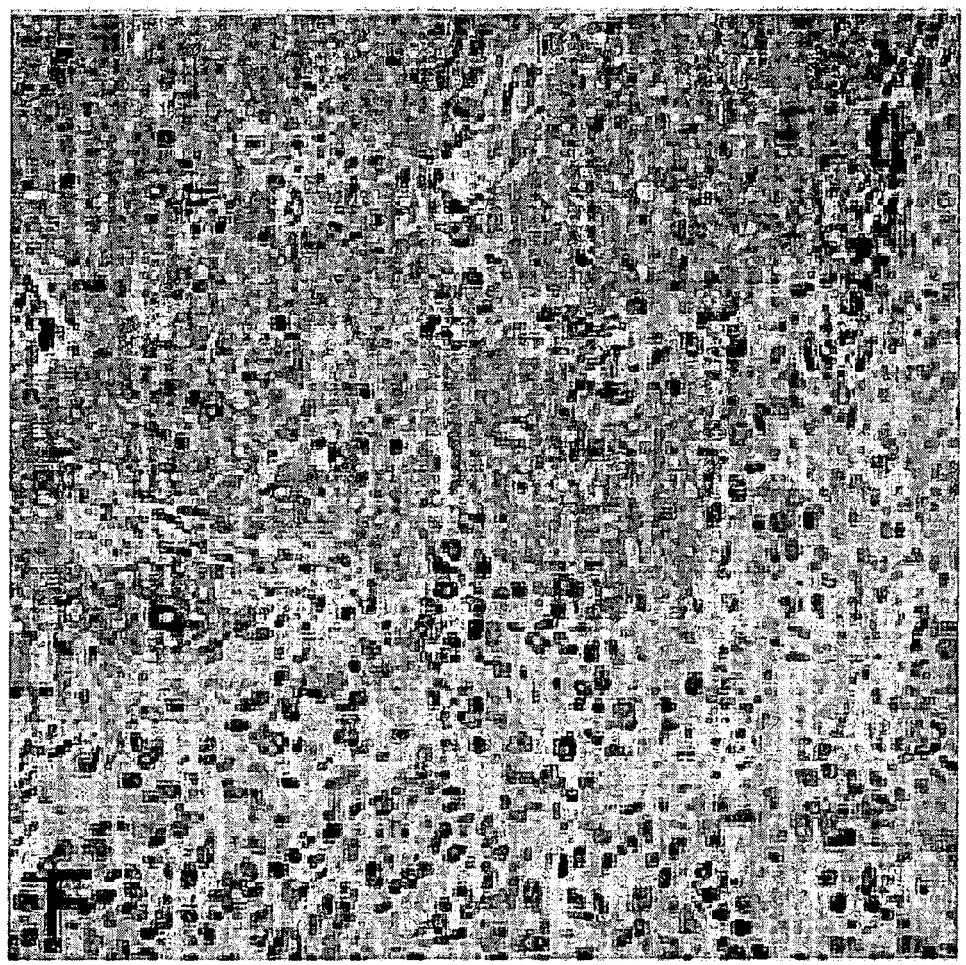
Figure 5G:
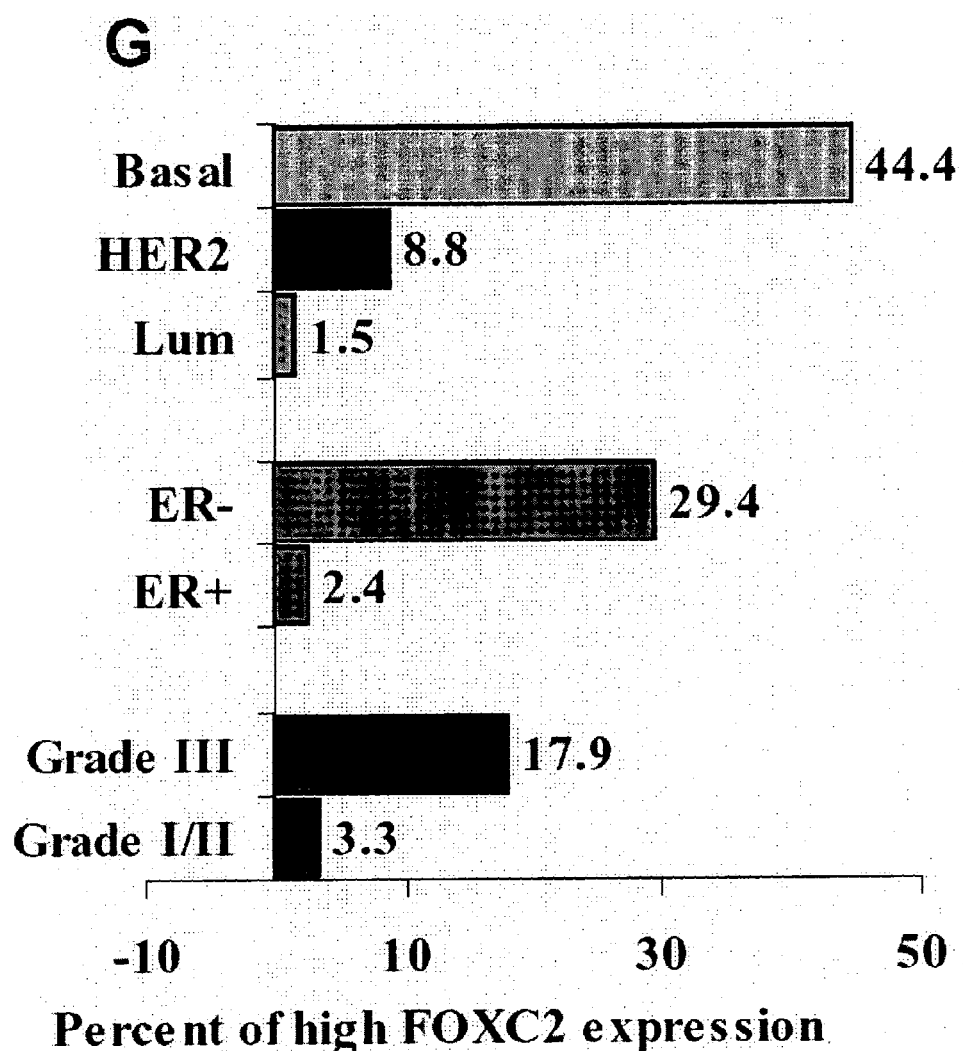

FIGS. 5A-5H show that FOXC2 is expressed at high level in human basal like breast cancer assessed by tissue microarray. FIGS. 5A-5F show representative immunohistochemical stains of FOXC2 in breast cancer tissue microarrays using anti-human FOXC2 antibody. A—Normal mammary gland, B—Negative tumor staining C—Weak cytoplasmic staining, D—Strong cytoplasmic staining, E—strong nuclear staining, F—Strong nuclear and cytoplasmic staining. FIG. 5G: Expression of FOXC2 in individual tumor samples plotted into groups based on the tumor type. Each bar represents the percentage of high expression in the respective tumor type relative to low expression and no expression. FIG. 5H: Table representing high FOXC2 expression compared to the total number of cases and the p-value.

Figure 6:
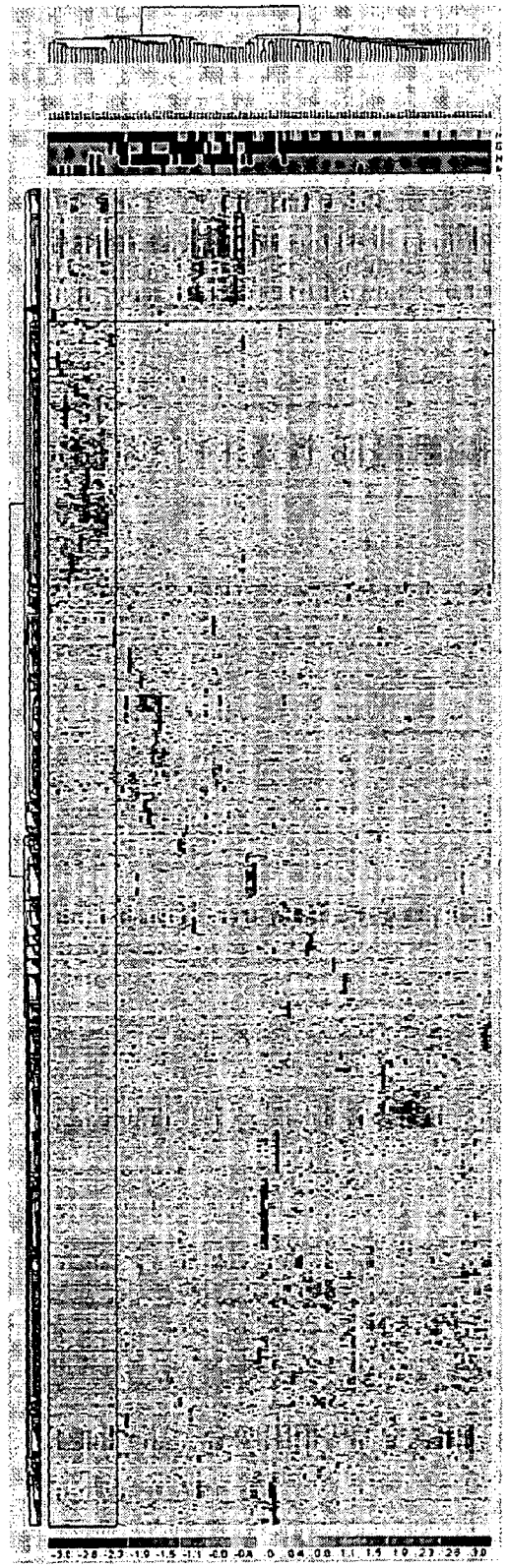

FIG. 6 shows tumor subtypes determined by hierarchical clustering of gene expression profiles. Hierarchical clustering of 117 sporadic invasive breast cancers, for 1350 non-redundant probe sets (genes) filtered for variable expression across the samples. Clustering orders the cancers according to greatest similarity of gene expression, shown by the dendogram at the top, and orders genes by similarity of expression level among the sample set, shown by the dendogram along the side.

Figure 7:
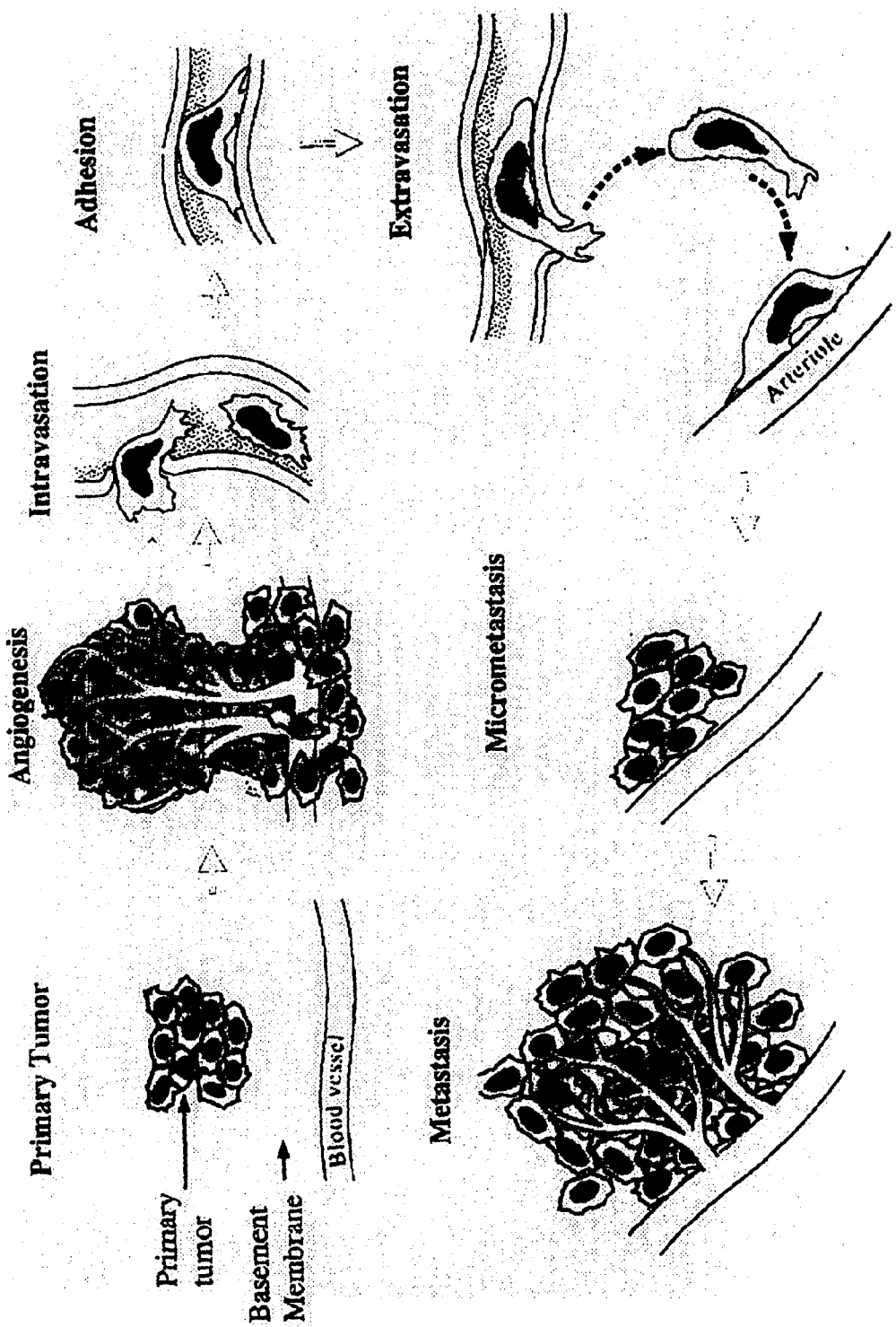

FIG. 7 shows a model of the steps involved in metastasis.

DETAILED DESCRIPTION OF THE INVENTION

I. Overview

Although the genetic basis of tumorigenesis may vary between different cancer types, the cellular and molecular mechanisms required for metastasis seems to be similar for all the solid tumor types. During a metastatic cascade, the cancer cells lose growth inhibitory response, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. The molecular mechanisms that drive invasion and metastasis are similar to those found in embryonic development, trophoblast implantation, and mammary gland development.

More than 90% of all cancers are of epithelial tissue origin and these epithelial cancer cells are attached to one another via cell-cell adhesion molecules, such that these cells are non-motile. In order for these epithelial cells to become motile, they need to loosen the cell-cell adhesion and acquire fibroblastic properties through a process called epithelial-mesenchymal transition (EMT). This process is similar to the formation of neural crest cells during development by EMT except that these neural crest cells migrate to different parts of the body and give rise to variety of mesenchymal tissues, whereas the tumor cells migrate to different parts of the body and forms epithelial-looking tumors. EMT in cancer is proposed to be transient because the metastatic nodules posses all the characteristic of the primary tumor from which they originated.

It has been proposed that, once cancer cells reach the distant site, they undergo a mesenchymal-epithelial transition (MET). EMT and MET are highly conserved and fundamental process that govern morphogenesis in multicultural organisms. One EMT marker, S100A4/FSP, was recently shown to play functional role in determining the latency of tumor progression suggesting that EMT might be playing important role in tumor progression.

Applicants have performed a screen using DNA microarray gene analysis of mouse mammary cancer cell lines, established from a BALB/c mammary tumor by Fred Miller, to identify genes involved in the regulation of metastasis. Using this approach, Applicants have identified several metastasis candidate genes that were overexpressed in a highly metastatic cell line. However, one of the candidate gene, Mesenchyme Forkhead 1, also known as FOXC2, was overexpressed at very high levels in the metastatic cell line. In addition, Applicants have found that FOXC2 is also overexpressed in highly aggressive sub-type of human breast cancer called basal like breast cancer.

The amino acid sequence and the cDNA sequence of human FOXC2, also called FREAC 11 or FKHL14, is described in International PCT Publication No. WO 98/54216, and in Miura et al. (1997) Genomics, 41: 489-492, the teachings of which are hereby incorporated by reference in their entirety. In addition, the mouse form of FOXC2 is referred to as Fkh1/Mf1 in the art. Sequences of the mouse FOXC2 gene may be found in Miura et al. (1993) FEBS letters 326:171-176. Additional sequences may be found in International PCT Publication WO01/60853, Genbank Accession No. NP_005242 (Protein) and Genbank Accession No. NM_005251 (mRNA sequence).

Applicants have tested if the association of high FOXC2 expression/function is causally associated with metastasis by performing ectopic expression experiments with FOXC2. Applicants have discovered that when FOXC2 is overexpressed in epithelial cells, EMT is induced, concomitant with increased migration and invasion. Furthermore, when FOXC2 is overexpressed by Applicants in the non-metastatic breast cancer cell line EpHRas, the cell line becomes metastatic. Applicants have also discovered that FOXC2 lies downstream to all genes tested which are capable of inducing EMT. Based in part on this discovery, applicants have invented novel methods of treating, preventing and diagnosing cancer metastasis using FOXC2.

Accordingly, one aspect of the invention provides a method of modulating metastasis. In one specific aspect, the invention provides a method of decreasing metastasis by a cell, the method comprising contacting the cell with an agent that decreases FOXC2 gene expression or FOXC2 activity, such as a FOXC2 antagonist. In some embodiments of this method, the cell is in a metazoan, such as in a mammal or in a human. Similarly, another aspect of the invention provides a method of treating or preventing metastasis in an individual in need thereof, the method comprising administering to an individual a therapeutically effective amount of an agent which decreases FOXC2 gene expression or FOXC2 activity, such as a FOXC2 antagonist. In some embodiments, the individual is afflicted with a hyperplastic condition, such as an individual afflicted with a tumor or with a cancer. In some embodiments of the methods for preventing metastasis in an individual, the individual has already undergone a first treatment for a hyperplastic condition to remove or kill a tumor prior to the administration of the FOXC2 antagonist. In such embodiments, the FOXC2 antagonist may prevent any residual tumor cells or residual precancerous cells which may have survived the first treatment from metastasizing.

The methods described herein for the treatment or prevention of metastasis by a cell or in an individual are not limited to any particular type of cell or hyperplastic condition. In some embodiments, the cell is an epithelial cell, or the cancer that is being treated or prevented is of epithelial origin. In some embodiments, the cancer is breast cancer, lung cancer or skin cancer.

The agents which inhibit FOXC2 expression or activity include, but are not limited to, polypeptides, nucleic acids, antibodies and small molecules, such as having a molecular weight less than 1 kDa. In some embodiments, the agents comprise nucleic acids. In some embodiments, the nucleic acids comprise antisense reagents, such as siRNAs or small hairpin RNAs directed to inhibit FOXC2 gene expression. In other embodiments, the agents comprise nucleic acids encoding such agents, such as viruses, like adenoviruses, which comprise such nucleic acids. In other embodiments, the agents comprise nucleic acids which encode fragments or mutant forms of FOXC2 which antagonize the function of endogenous FOXC2 in a cell. Such mutant forms include for example, fragments which compete with the endogenous FOXC2 for DNA binding, such as to bind promoter regions of genes that are transcriptionally regulated by FOXC2, or fragments or mutants which compete with FOXC2 for binding to FOXC2 interacting proteins. International PCT publication No. WO 03/064467 describes FOXC2 interacting proteins, including p621, NOLP, HSC71, FTP3, CLH1 AKAP. FOXC2 promoter blockers.

The invention further provides agents and compositions for use in the treatment and prevention of cancer and of cancer metastasis. One aspect of the invention provides a composition for use in inhibiting metastasis comprising a) a FOXC2 antagonist; and b) a suitable carrier.

The invention also provides methods of identifying agents which inhibit metastasis. In one aspect, these methods comprise the identification of agents which inhibit the expression of a FOXC2 gene product, such as a FOXC2 mRNA or a FOXC2 polypeptide in a cell. Any standard techniques more measuring gene expression may be used in combination with the methods described herein. Related methods provided herein comprise measuring the expression of a reporter gene operably linked to a FOXC2 promoter in a cell, such that candidates agents which when contacted with the cell decrease expression of the reporter gene are identified as agents capable of inhibiting metastasis. Nucleic acids comprising FOXC2 promoters and methods of identifying agents which regulate expression of a gene which is operably linked to said promoters, are described in U.S. Patent Publication No. 2002/0090707, the entire teachings of which are herein incorporated by reference.

The invention relates to a method of predicting the likelihood of development of a metastatic condition in an individual, e.g., a human. In one embodiment, the method comprises the steps of obtaining a biological sample from a mammal to be tested; determining the level of a FOXC2 gene product in the sample (i.e., the test level); and comparing the test level with an appropriate control, wherein if the test level is greater than the level of the gene product in a normal sample, then the mammal has an increased likelihood of developing a metastatic condition. The invention provides a method of determining if an individual is at risk for developing cancer metastasis, the method comprising (a) obtaining a nucleic acid sample from the individual; and (b) determining if the nucleic sample contains mutations in the FOXC2 gene which results in increase FOXC2 expression or activity, wherein the presence of such mutation indicates that the individual is at risk of developing cancer metastasis.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The term "expression vector" and equivalent terms are used herein to mean a vector which is capable of inducing the expression of DNA that has been cloned into it after transformation into a host cell. The cloned DNA is usually placed under the control of (i.e., operably linked to) certain regulatory sequences such a promoters or enhancers. Promoters sequences maybe constitutive, inducible or repressible.

The term "operably linked" is used herein to mean molecular elements that are positioned in such a manner that enables them to carry out their normal functions. For example, a gene is operably linked to a promoter when its transcription is under the control of the promoter and, if the gene encodes a protein, such transcription produces the protein normally encoded by the gene. For example, a binding site for a transcriptional regulator is said to be operably linked to a promoter when transcription from the promoter is regulated by protein(s) binding to the binding site. Likewise, two protein domains are said to be operably linked in a protein when both domains are able to perform their normal functions.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

An "individual" to be treated by the method of the invention can mean either a human or non-human animal, preferably a mammal.

The term "encoding" comprises an RNA product resulting from transcription of a DNA molecule, a protein resulting from the translation of an RNA molecule, or a protein resulting from the transcription of a DNA molecule and the subsequent translation of the RNA product.

The term "promoter" is used herein to mean a DNA sequence that initiates the transcription of a gene. Promoters are typically found 5' to the gene and located proximal to the start codon. If a promoter is of the inducible type, then the rate of transcription increases in response to an inducer. Promoters may be operably linked to DNA binding elements that serve as binding sites for transcriptional regulators. The term "mammalian promoter" is used herein to mean promoters that are active in mammalian cells. Similarly, "prokaryotic promoter" refers to promoters active in prokaryotic cells.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The term "recombinant" is used herein to mean any nucleic acid comprising sequences which are not adjacent in nature. A recombinant nucleic acid may be generated in vitro, for example by using the methods of molecular biology, or in vivo, for example by insertion of a nucleic acid at a novel chromosomal location by homologous or non-homologous recombination.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "microarray" refers to an array of distinct polynucleotides or oligonucleotides synthesized on a substrate, such as paper, nylon or other type of membrane, filter, chip, glass slide, or any other suitable solid support.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The terms "level of expression of a gene in a cell" or "gene expression level" refer to the level of mRNA, as well as pre-mRNA nascent transcript(s), transcript processing intermediates, mature mRNA(s) and degradation products, encoded by the gene in the cell.

The term "modulation" refers to upregulation (i.e., activation or stimulation), downregulation (i.e., inhibition or suppression) of a response, or the two in combination or apart. A "modulator" is a compound or molecule that modulates, and may be, e.g., an agonist, antagonist, activator, stimulator, suppressor, or inhibitor.

The term "prophylactic" or "therapeutic" treatment refers to administration to the individual of one or more of the individual compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

The term "effective amount" refers to the amount of a therapeutic reagent that when administered to an individual by an appropriate dose and regime produces the desired result.

The term "individual in need of treatment for a disorder" is an individual diagnosed with that disorder or suspected of having that disorder.

The term "recombinant" as used in reference to a nucleic acid indicates any nucleic acid that is positioned adjacent to one or more nucleic acid sequences that it is not found adjacent to in nature. A recombinant nucleic acid may be generated in vitro, for example by using the methods of molecular biology, or in vivo, for example by insertion of a nucleic acid at a novel chromosomal location by homologous or non-homologous recombination. The term "recombinant" as used in reference to a polypeptide indicates any polypeptide that is produced by expression and translation of a recombinant nucleic acid.

The following terms are used to describe the sequence relationships between two or more polynucleotides: "reference sequence," "comparison window," "sequence identity," "percentage of sequence identity," and "substantial identity." A reference sequence is a defined sequence used as a basis for a sequence comparison; a reference sequence can be a subset of a larger sequence, for example, as a segment of a fall length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides can each (1) comprise a sequence (for example a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A comparison window, as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window can comprise additions and deletions (for example, gaps) of 20 percent or less as compared to the reference sequence (which would not comprise additions or deletions) for optimal alignment of the two sequences. Optimal alignment of sequences for aligning a comparison window can be conducted by the local identity algorithm (Smith and Waterman, Adv. Appl. Math., 2:482 (1981)), by the identity alignment algorithm (Needleman and Wunsch, J. Mol. Bio., 48:443 (1970)), by the search for similarity method (Pearson and Lipman, Proc. Natl. Acid. Sci. U.S.A. 85:2444 (1988)), by the computerized implementations of these algorithms such as GAP, BESTFIT, FASTA and TFASTA (Wisconsin Genetics Software Page Release 7.0, Genetics Computer Group, Madison, Wis.), or by inspection. Preferably, the best alignment (for example, the result having the highest percentage of identity over the comparison window) generated by the various methods is selected.

The term "diagnostic" refers to assays that provide results which can be used by one skilled in the art, typically in combination with results from other assays, to determine if an individual is suffering from a disease or disorder of interest such as breast cancer, whereas the term "prognostic" refers to the use of such assays to evaluate the response of an individual having such a disease or disorder to therapeutic or prophylactic treatment. The term "pharmacogenetic" refers to the use of assays to predict which individual patients in a group will best respond to a particular therapeutic or prophylactic composition or treatment.

Other technical terms used herein have their ordinary meaning in the art that they are used, as exemplified by a variety of technical dictionaries, such as the McGraw-Hill Dictionary of Chemical Terms and the Stedman's Medical Dictionary.

III. Agents and Compositions

Another aspect of the invention provides agents and compositions for use in the treatment, diagnosis, prognosis and prevention of cancer and of cancer metastasis. One aspect of the invention provides a composition for use in inhibiting metastasis comprising: a) a FOXC2 antagonist; and b) a suitable carrier, such as a pharmaceutically or physiologically acceptable carrier. The term "FOXC2 antagonist" as used herein, refers to a molecule which blocks or reduces the expression or biological activity of a FOXC2 gene product. Antagonists may include proteins, nucleic acids, carbohydrates, or any other molecules which bind or interact with the a FOXC2 gene product.

In some embodiments, the compositions comprise additional agents with anticancer or antimetastatic properties. In some embodiments, the additional agent is a cytotoxic agent or an anti-angiogenic agent. In yet further embodiments, the FOXC2 antagonist is present in or conjugated onto a liposome or microparticle that is of a suitable size for intravenous administration but that lodges in capillary beds.

In some of embodiments of methods described herein, an agent which reduces the expression of FOXC2 comprises a double stranded RNAi molecule, a ribozyme, or an antisense nucleic acid directed at a FOXC2 nucleic acid. In one embodiment, the FOXC2 antagonist is a compound having a molecular weight less than 1 kDa, or more preferably less than 500 Daltons.

In some embodiments of the compositions or methods described herein, the FOXC2 antagonist comprises antisense nucleic acids which reduce the gene expression of FOXC2 by a process known RNA interference (RNAi). RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence.

For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of in some instances as few as 21 to 22 base pairs in length. Furthermore, RNAi may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates RNAse L, a nonspecific enzyme that targets all mRNAs. The nonspecific pathway may represents a host response to stress or viral infection, and, in general, the effects of the nonspecific pathway are preferably minimized under preferred methods of the present invention. Significantly, longer dsRNAs appear to be required to induce the nonspecific pathway and, accordingly, dsRNAs shorter than about 30 bases pairs are preferred to effect gene repression by RNAi (see Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

RNAi has been shown to be effective in reducing or eliminating the expression of a gene in a number of different organisms including Caenorhabditis elegans (see e.g. Fire et al. (1998) Nature 391: 806-11), mouse eggs and embryos (Wianny et al. (2000) Nature Cell Biol 2: 70-5; Svoboda et al. (2000) Development 127: 4147-56), and cultured RAT-1 fibroblasts (Bahramina et al. (1999) Mol Cell Biol 19: 274-83), and appears to be an anciently evolved pathway available in eukaryotic plants and animals (Sharp (2001) Genes Dev. 15: 485-90). RNAi has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass (2001) Nature 411: 428-9). In mammalian cells, siRNAs are effective at concentrations that are several orders of magnitude below the concentrations typically used in antisense experiments (Elbashir et al. (2001) Nature 411: 494-8).

The double stranded oligonucleotides used to effect RNAi of FOXC2 are preferably less than 30 base pairs in length and, more preferably, comprise about 29, 28, 27, 26, 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art (e.g. Expedite RNA phophoramidites and thymidine phosphoramidite (Proligo, Germany). Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. For example, any of the above RNA species will be designed to include a portion of nucleic acid sequence of the FOXC2 gene.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing-programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions of the invention.

The dsRNA oligonucleotides may be introduced into the cell by transfection with an heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. Further compositions, methods and applications of RNAi technology are provided in U.S. Pat. Nos. 6,278,039, 5,723,750 and 5,244,805, which are incorporated herein by reference.

Ribozyme molecules designed to catalytically cleave FOXC2 mRNA transcripts can also be used to prevent translation of FOXC2 (see, e.g., PCT International Publication WO90/11364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to the gene whose activity is to be reduced.

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach (1988) Nature 334:585-591; and see PCT Appln. No. WO89/05852, the contents of which are incorporated herein by reference). Hammerhead ribozyme sequences can be embedded in a stable RNA such as a transfer RNA (tRNA) to increase cleavage efficiency in vivo (Perriman et al. (1995) Proc. Natl. Acad. Sci. USA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617-27; Koseki et al. (1999) J Virol 73: 1868-77; Kuwabara et al. (1999) Proc Natl Acad Sci USA 96: 1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

In addition, ribozymes possess highly specific endoribonuclease activity, which autocatalytically cleaves the target sense mRNA. The present invention extends to ribozymes which hybridize to a sense mRNA encoding FOXC2 or any other genes of interest described herein, thereby hybridizing to the sense mRNA and cleaving it, such that it is no longer capable of being translated to synthesize a functional polypeptide product.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324: 429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In a long target RNA chain, significant numbers of target sites are not accessible to the ribozyme because they are hidden within secondary or tertiary structures (Birikh et al. (1997) Eur J Biochem 245: 1-16). To overcome the problem of target RNA accessibility, computer generated predictions of secondary structure are typically used to identify targets that are most likely to be single-stranded or have an "open" configuration (see Jaeger et al. (1989) Methods Enzymol 183: 281-306). Other approaches utilize a systematic approach to predicting secondary structure which involves assessing a huge number of candidate hybridizing oligonucleotides molecules (see Milner et al. (1997) Nat Biotechnol 15: 537-41; and Patzel and Sczakiel (1998) Nat Biotechnol 16: 64-8). Additionally, U.S. Pat. No. 6,251,588, the contents of which are hereby incorporated herein, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the RNAi oligonucleotides and ribozymes of the invention.

In some embodiments of the compositions or methods described herein, the FOXC2 antagonist comprises an antibody or fragment thereof, such as an antibody which binds and inhibits the function of FOXC2. The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2,Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

Chickens, mammals, such as a mouse, a hamster, a goat, a guinea pig or a rabbit, can be immunized with an immunogenic form of the FOXC2, or any polypeptide provided by the invention, or with peptide variants thereof (e.g., an antigenic fragment which is capable of eliciting an antibody response). Techniques for conferring immunogenicity on a protein or peptide include conjugation to carriers or other techniques well known in the art. For instance, a peptidyl portion of one of the individual proteins can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, antisera can be obtained and, if desired, polyclonal antibodies against the target protein can be further isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature, 256: 495-497, 1975), as well as the human B cell hybridoma technique (Kozbar et al., Immunology Today, 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive to the peptide immunogen and the monoclonal antibodies isolated. Accordingly, another aspect of the invention provides hybridoma cell lines which produce the antibodies described herein. The antibodies can then be tested for their effects on the activity and expression of the protein to which they are directed.

In some embodiments, the FOXC2 antibody is conjugated to a cytotoxic agent. In one embodiment, the cytotoxic agent is selected from the group consisting of nitrogen mustards, gemcitabine, ethylenimine derivatives, alkyl sulfonates, nitrosoureas, triazenes, folic acid analogs, anthracyclines, taxanes, SN-38, COX-2 inhibitors, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, doxorubicins and their analogs, antimetabolites, alkylating agents, antimitotics, antiangiogenic, apoptotoic agents and methotrexate, CPT-11.

In yet another embodiment of the compositions or methods described herein, the agent or the FOXC2 antagonist is a polypeptide, such as a FOXC2 polypeptide, or a fragment thereof, which antagonizes a biological activity of endogenous FOXC2 in a cell. In one embodiment, the agent is a mutant FOXC2 polypeptide which inhibits endogenous FOXC2 protein activity. Examples of such inhibitory agents include a nucleic acid molecule encoding a dominant negative FOXC2 a protein, such as a fragment of FOXC2 which competes with a naturally occurring FOXC2 protein for DNA binding but which is unable to activate transcription of target genes.

In another specific embodiment, the FOXC2 antagonist comprises a polypeptide having a DNA binding domain capable of binding to promoters to which FOXC2 normally binds. Such antagonist may comprises at least one zinc-finger. Methods are known in the art for designing DNA binding proteins which bind to specific DNA sequences, including those disclosed in U.S. Pat. Nos. 6,607,882, 6,453,242 and 6,511,808. In other embodiments, the FOXC2 antagonists comprise nucleic acids encoding the polypeptides which inhibit the function of FOXc2.

Another aspect of the invention provides a composition for use in inhibiting metastasis comprising: (i) a FOXC2 antagonist; (b) an antineoplastic agent; and (iii) a pharmaceutically or physiologically acceptable carrier. Antineoplastic agents include, but are not limited to, chemical compounds, drugs, an antibodies or derivative thereof and RNAi reagents. Antineoplastic agents include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alpha, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

In one embodiment, the antineoplastic agent is 5-Fluorouracil, 6-mercatopurine, Actinomycin, Adriamycin®, Adrucil®, Aminoglutethimide, Anastrozole, Aredia®, Arimidex®, Aromasin®, Bonefos®, Bleomycin, carboplatin, Cactinomycin, Capecitabine, Cisplatin, Clodronate, Cyclophosphamide, Cytadren®, Cytoxan®, Dactinomycin, Docetaxel, Doxorubicin, Epirubicin, Etoposide, Exemestane, Femara®, Fluorouracil, Fluoxymesterone, Halotestin®, Herceptin®, Letrozole, Leucovorin calcium, Megace®, Megestrol acetate, Methotrexate, Mitomycin, Mitoxantrone, Mutamycin®, Navelbine®, Nolvadex®, Novantrone®, Oncovin®, Ostac®, Paclitaxel, Pamidronate, Pharmorubicin®, Platinol®, prednisone, Procytox®, Tamofen®, Tamone®, Tamoplex®, Tamoxifen, Taxol®, Taxotere®, Trastuzumab, Thiotepa, Velbe®, Vepesid®, Vinblastine, Vincristine, Vinorelbine, Xeloda®, or a combination thereof.

In another embodiment, the antineoplastic agent comprises a monoclonal antibody, a humanized antibody, a chimeric antibody, a single chain antibody, or a fragment of an antibody. Exemplary antibodies include, but are not limited to, Rituxan, IDEC-C2B8, anti-CD20 Mab, Panorex, 3622W94, anti-EGP40 (17-1A) pancarcinoma antigen on adenocarcinomas Herceptin, Erbitux, anti-Her2, Anti-EGFr, BEC2, anti-idiotypic-GD$_3$ epitope, Ovarex, B43.13, anti-idiotypic CA125, 4B5, Anti-VEGF, RhuMAb, MDX-210, anti-HER2, MDX-22, MDX-220, MDX-447, MDX-260, anti-GD-2, Quadramet, CYT-424,IDEC-Y2B8, Oncolym, Lym-1, SMART M195, ATRAGEN, LDP-03, anti-CAMPATH, for t6, anti CD6, MDX-11, OV103, Zenapax, Anti-Tac, anti-IL-2 receptor, MELIMMUNE-2, MELIMMUNE-1, CEACIDE, Pretarget, NovoMAb-G2, TNT, anti-histone, Gliomab-H, GNI-250, EMD-72000, LymphoCide, CMA 676, Monopharm-C, anti-FLK-2, SMART 1D10, SMART ABL 364, ImmuRAIT-CEA, or combinations thereof.

In another embodiment, the antineoplastic agent is an antibody selected from the group consisting of Rituxan, IDEC-C2B8, anti-CD20 Mab, Panorex, 3622W94, anti-EGP40 (17-1A) pancarcinoma antigen on adenocarcinomas Herceptin, Erbitux, anti-Her2, Anti-EGFr, BEC2, anti-idiotypic-GD$_3$ epitope, Ovarex, B43.13, anti-idiotypic CA125, 4B5, Anti-VEGF, RhuMAb, MDX-210, anti-HER2, MDX-22, MDX-220, MDX-447, MDX-260, anti-GD-2, Quadramet, CYT-424, IDEC-Y2B8, Oncolym, Lym-1, SMART M195, ATRAGEN, LDP-03, anti-CAMPATH, anti CD6, MDX-11, OV103, Zenapax, Anti-Tac, anti-IL-2 receptor, MELIMMUNE-2, MELIMMUNE-1, CEACIDE, Pretarget, NovoMAb-G2, TNT, anti-histone, Gliomab-H, GNI-250, EMD-72000, LymphoCide, CMA 676, Monopharm-C, anti-FLK-2, SMART 1D10, SMART ABL 364, and ImmuRAIT-CEA.

In another embodiment, the antineoplastic agent comprises an antibody, or fragment thereof, specific for a tumor antigen, such as a tumor antigen selected from the group consisting of HER2/neu, CA15.3, CD31, CD105, Tie-2/Tek, NY-ESO-1, MTA1 and MUC1.

In yet another embodiment, the antineoplastic agent comprises a fixed or non-replicating tumor cell which may be used as a cancer vaccine to elicit an immune response in the subject. In a specific embodiment, the additional type of tumor cell is a MCF-10A, MCF-10F, MCF-10-2A, MCF-12A, MCF-12F, ZR-75-1, ZR-75-30, UACC-812, UACC-893, HCC38, HCC70, HCC202, HCC1007 BL, HCC1008, HCC1143, HCC1187, HCC1187 BL, HCC1395, HCC1569, HCC1599, HCC1599 BL, HCC1806, HCC1937, HCC1937 BL, HCC1954, HCC1954 BL, HCC2157 , Hs 274.T, Hs 281.T, Hs 343.T, Hs 362.T, Hs 574.T, Hs 579.Mg, Hs 605.T, Hs 742.T, Hs 748.T, Hs 875.T, MB 157, SW527, 184A1, 184B5, MDA-MB-330, MDA-MB-415, MDA-MB-435S, MDA-MB-436, MDA-MB-453, MDA-MB-468 RT4, BT-474, CAMA-1, MCF7 [MCF-7], MDA-MB-134-VI, MDA-MB-157, MDA-MB-175-VII HTB-27 MDA-MB-361, SK-BR-3 or ME-180 cell, all of which are available from ATTC.

In another embodiment, the antineoplastic agent comprises a tumor antigen. In one specific embodiment, the tumor antigen is her2/neu. Tumor antigens are well-known in the art and are described in U.S. Pat. Nos. 4,383,985 and 5,665,874, in U.S. Patent Publication No. 2003/0027776, and International PCT Publications Nos. WO00/55173, WO00/55174, WO00/55320, WO00/55350 and WO00/55351.

In another embodiment, the antineoplastic agent comprises an antisense reagent, such as an siRNA or a hairpin RNA molecule, which reduces the expression or function of a gene that is expressed in a cancer cell. Exemplary antisense reagents which may be used include those directed to mucin, Ha-ras, VEGFR1 or BRCA1. Such reagents are described in U.S. Pat. Nos. 6,716,627 (mucin), 6,723,706 (Ha-ras), 6,710,174 (VEGFR1) and in U.S. Patent Publication No. 2004/0014051 (BRCA1).

In one embodiment, the compositions described herein are pharmaceutical compositions. Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, by aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery.

An exemplary composition of the invention comprises an compound capable of inhibiting the expression or activity of FOXC2, such as a FOXC2 dominant-negative polypeptide, a anti-FOXC2 antibody or a FOXC2 antisense reagent, with a delivery system, such as a liposome system, and optionally including an acceptable excipient. In a preferred embodiment, the composition is formulated for injection.

Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlomtetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In the therapeutic methods described herein, FOXC2 inhibitors can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection. The FOXC2 inhibitors of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, oligomers may be formulated into ointments, salves, gels, or creams as generally known in the art. In some embodiments, the FOXC2 inhibitors may be administered locally at the site of a tumor, such as by injection into the tumor tissue, or by implantation of a formulation at or near the site of a tumor.

Toxicity and therapeutic efficacy of the agents and compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of the methods described herein, the effective amount of the agent is between about 1 mg and about 50 mg per kg body weight of the individual. In one embodiment, the effective amount of the agent is between about 2 mg and about 40 mg per kg body weight of the individual. In one embodiment, the effective amount of the agent is between about 3 mg and about 30 mg per kg body weight of the individual. In one embodiment, the effective amount of the agent is between about 4 mg and about 20 mg per kg body weight of the individual. In one embodiment, the effective amount of the agent is between about 5 mg and about 10 mg per kg body weight of the individual.

In one embodiment of the methods described herein, the agent is administered at least once per day. In one embodiment, the agent is administered daily. In one embodiment, the agent is administered every other day. In one embodiment, the agent is administered every 6 to 8 days. In one embodiment, the agent is administered weekly.

As for the amount of the compound and/or agent for administration to the individual, one skilled in the art would know how to determine the appropriate amount. As used herein, a dose or amount would be one in sufficient quantities to either inhibit the disorder, treat the disorder, treat the individual or prevent the individual from becoming afflicted with the disorder. This amount may be considered an effective amount. A person of ordinary skill in the art can perform simple titration experiments to determine what amount is required to treat the individual. The dose of the composition of the invention will vary depending on the individual and upon the particular route of administration used. In one embodiment, the dosage can range from about 0.1 to about 100,000 ug/kg body weight of the individual. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

The effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount. In one embodiment of the above methods, the effective amount of the compound comprises from about 1.0 ng/kg to about 100 mg/kg body weight of the individual. In another embodiment of the above methods, the effective amount of the compound comprises from about 100 ng/kg to about 50 mg/kg body weight of the individual. In another embodiment of the above methods, the effective amount of the compound comprises from about 1 ug/kg to about 10 mg/kg body weight of the individual. In another embodiment of the above methods, the effective amount of the compound comprises from about 100 ug/kg to about 1 mg/kg body weight of the individual.

As for when the compound, compositions and/or agent is to be administered, one skilled in the art can determine when to administer such compound and/or agent. The administration may be constant for a certain period of time or periodic and at specific intervals. The compound may be delivered hourly, daily, weekly, monthly, yearly (e.g. in a time release form) or as a one time delivery. The delivery may be continuous delivery for a period of time, e.g. intravenous delivery. In one embodiment of the methods described herein, the agent is administered at least once per day. In one embodiment of the methods described herein, the agent is administered daily. In one embodiment of the methods described herein, the agent is administered every other day. In one embodiment of the methods described herein, the agent is administered every 6 to 8 days. In one embodiment of the methods described herein, the agent is administered weekly.

IV. Methods of Preventing/Treating Disease

Some aspects of the invention provide methods of treating or preventing cancer, or of treating and preventing metastasis of tumors. Related aspects of the invention provide methods of preventing, aiding in the prevention, and/or reducing metastasis of hyperplastic or tumor cells in an individual.

One aspect of the invention provides a method of inhibiting metastasis in an individual in need thereof, the method comprising administering to the individual an effective metastasis-inhibiting amount of a FOXC2 antagonist. The invention further provides a method of inhibiting metastasis in an individual in need thereof, the method comprising administering to the individual an effective metastasis-inhibiting amount of any one of the compositions described herein which comprise a FOXC2 antagonist.

In some embodiments of the methods for inhibiting metastasis in an individual in need thereof, a second agent is administered to the individual, such as an antineoplastic agent. In some embodiments, the second agent comprises a second metastasis-inhibiting agent, such as a CD26 antagonist, a plasminogen antagonist, or an adenosine deaminase antagonist. In other embodiments, the second agent is an angiogenesis inhibiting agent.

In further embodiments, the second agent is an anticancer agent, such as an agent selected from the group consisting of cisplatin, carboplatin, oxaliplatin, radiation, CPT-11, paclitaxel, 5-flourouracil, leucovorin, epothilone, gemcitabine, UFT, herceptin, cytoxan, dacarbaxine, ifosfamide, mechlorethamine, melphalan, chlorambucil, anastrozole and exemstane, carmustine, lomustine, methotrexate, gemcitabine, cytarabine, fludarabine, bleomycin, dactinomycin, daunorubicin, doxorubicin, idarubicin, docetaxel, 5 vinblastine, vincristin, vinorelbine, topotecan, lupron, megace, leucovorin, Iressa, flavopiridol, immunomotherapeutic agents, ZD6474, SU6668, and valspodar.

In some embodiments of the methods for inhibiting or treating metastasis in an individual in need thereof, the FOXC2 antagonist is administered intravenously, intramuscularly, intradermally or subcutaneously. The methods of the invention are not limited to a particular form of administration. In some specific embodiments, the agent is administered locally at to a region of the body which contains a tumor or cancer. For instance, if an individual is afflicted with breast cancer, the agent may be administered systemically or directly to the breasts. In some embodiments, a tumor is surgically removed, and the agent is administered locally to the site of tumor excision to prevent metastasis of any remaining tumor cells, or of pretumor cells which are at high risk of developing into tumor tissue. In some embodiments, the agent is embedded within or associated with a matrix and implanted into the individual, preferably at or near the site of cancer or tumor growth.

In some embodiments of the methods for inhibiting or treating metastasis in an individual in need thereof, the individual is afflicted with a hyperplastic condition, such as with cancer or with a tumor. The methods described herein are not limited to any particular hyperplastic condition. In specific embodiments, the individual is afflicted with at least one form of renal cell cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, gastrointestinal cancer, or stomach cancer, or a combination thereof. In some embodiments, the individual is afflicted with one form of cancer that has metastasized to at least another tissue. For example, the individual may be afflicted with one form of breast cancer, such as basal like breast cancer, wherein breast cancer cells have metastasized to the liver or to the lungs.

The individual in need of the described treatment can be at risk for a metastatic condition, either genetically (e.g., through heredity) or environmentally, or the mammal can have one or more non-metastatic tumors. For example, the mammal can be at risk for or currently have one or more non-metastatic conditions selected from the group consisting of melanoma, breast cancer, ovarian cancer, prostate cancer, lung cancer, bone cancer, throat cancer, brain cancer, testicular cancer, liver cancer, stomach cancer, pancreatic cancer, and combinations thereof. Thus, the described treatment can be administered prophylactically or therapeutically. The described treatment can also be administered to a mammal having a metastatic condition to inhibit further metastasis.

In one embodiments of the methods described herein directed to the treatment of cancer metastasis, the subject is treated prior to, concurrently with, or subsequently to the treatment with the FOXC2 antagonists of the present invention, with a complementary therapy to for the cancer, such as surgery, chemotherapy, radiation therapy, or hormonal therapy or a combination thereof.

V. Methods of Diagnosing Metastasis

The invention relates, in part, to methods and reagents for diagnosing and aiding in the diagnosis of cancer metastasis, assessing the likelihood of developing a cancer metastasis and assessing the prognosis of cancer metastasis. The invention also provides a simple serological assay that may be used to predict, or aid in predicting, whether an individual is likely to develop a cancer metastasis, which makes it possible to provide treatment or further diagnostic testing. Thus, the invention relates to a method for predicting the likelihood that an individual will develop or will have in the future a cancer metastasis, a method for diagnosing or aiding in the diagnosis of a cancer metastasis, and a method of predicting the likelihood of having symptoms associated with a cancer metastasis. The present invention makes it possible to identify individuals at increased risk of developing cancer metastasis, such as but not limited to, breast cancer metastasis, and provide treatment to prevent such events or reduce their severity.

The invention further provides a method of predicting the likelihood, or aiding in predicting the likelihood, that a tumor individual (e.g. a human) will experience a cancer metastasis. In one embodiment, the method comprises obtaining a biological sample from an individual to be assessed for the likelihood of developing such a condition; determining the level of a FOXC2 gene product in the sample (i.e., the test level) and comparing the test level with a control level, wherein if the test level is greater than the level of the gene product in a control sample, the individual has an increased likelihood of developing metastasis. The control can be a sample from a tumor that is not metastatic.

A related aspect of the invention is a method of diagnosing a cancer metastasis in an individual, the method comprising (a) determining the level of a FOXC2 gene product in a tumor sample obtained from the individual; and (b) comparing the level determined in step (a) with the level of gene product in a control level, wherein if the level determined in (a) is greater than the level of gene product in the control level, the individual is determined to have the cancer metastasis.

The phrase "predicting the likelihood of developing" as used herein refers to methods by which the skilled artisan can predict onset of a cancer metastasis or event in an individual. The term "predicting" does not refer to the ability to predict the outcome with 100% accuracy. Instead, the skilled artisan will understand that the term "predicting" refers to forecast of an increased or a decreased probability that a certain outcome will occur; that is, that an outcome is more likely to occur in an individual exhibiting elevated FOXC2 levels in a tumor.

The invention further relates to a method of predicting the likelihood of development of a metastatic condition in a mammal, e.g., a human. In one embodiment, the method comprises the steps of obtaining a biological sample from a mammal to be tested; determining the level of a FOXC2 gene product in the sample (i.e., the test level); and comparing the test level with an appropriate control, wherein if the test level is greater than the level of the gene product in a normal sample, then the mammal has an increased likelihood of developing a metastatic condition. The control can be a sample from a normal mammal or a sample from a mammal having a metastatic condition. In one embodiment, the biological sample is a blood sample or a cell sample from a tumor in the mammal.

In one embodiment of the methods described herein, determining a level of a FOXC2 gene product in a biological sample obtained from an individual comprises determining the level of FOXC2 mRNA in the sample. The level of FOXC2 mRNA in the sample can be assessed by combining oligonucleotide probes derived from the nucleotide sequence of FOXC2 with a nucleic acid sample from the individual, under conditions suitable for hybridization. Hybridization conditions can be selected such that the probes will hybridize only with the specified gene sequence. In one specific embodiment, conditions can be selected such that the probes will hybridize only with an altered nucleotide sequences, such as but not limited to, splice isoforms, and not with unaltered nucleotide sequences; that is, the probes can be designed to recognize only particular alterations in the nucleic acid sequence of FOXC2, including addition of one or more nucleotides, deletion of one or more nucleotides or change in one or more nucleotides (including substitution of a nucleotide for one which is normally present in the sequence). In one specific embodiment, the oligonucleotide probe hybridizes to the FOXC2 mRNA sequence set forth as Genbank Deposit No. NM_005251, or to the coding region of the mRNA sequence.

Methods of quantitating mRNA in a sample are well-known in the art. In a particular embodiment, oligonucleotide probes specific to FOXC2 can be displayed on an oligonucleotide array or used on a DNA chip, as described in WO 95/11995. The term "microarray" refers to an array of distinct polynucleotides or oligonucleotides synthesized on a substrate, such as paper, nylon or other type of membrane, filter, chip, glass slide, or any other suitable solid support. Microarrays also includes protein microarrays, such as protein microarrays spotted with antibodies. Other techniques for detecting FOXC2 mRNA levels in a sample include reverse transcription of mRNA, followed by PCR amplification with primers specific for a FOXC2 mRNA.

In another embodiment of the methods described herein, determining a level of a FOXC2 gene product in a biological sample obtained from an individual comprises determining the level of FOXC2 polypeptide in the sample. The level of a FOXC2 gene product can be determined by contacting the sample with an antibody which specifically binds to FOXC2 and determining the amount of bound antibody, e.g., by detecting or measuring the formation of the complex between the antibody and a FOXC2 polypeptide. The antibodies can be labeled (e.g., radioactive, fluorescently, biotinylated or HRP-conjugated) to facilitate detection of the complex. Appropriate assay systems for detecting FOXC2 polypeptide levels include, but are not limited to, Enzyme-Linked Immunosorbent Assay (ELISA), competition ELISA assays, Radioimmuno-Assays (RIA), immunofluorescence, western, and immunohistochemical assays which involve assaying a FOXC2 gene product in a sample using antibodies having specificity for FOXC2. Numerous methods and devices are well known to the skilled artisan for the detection and analysis of FOXC2 of the instant invention. With regard to polypeptides or proteins in test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. These devices and methods can utilize labeled molecules in various sandwich, competitive, or non-competitive assay formats, to generate a signal that is related to the presence or amount of an analyte of interest. Additionally, certain methods and devices, such as but not limited to, biosensors and optical immunoassays, may be employed to determine the presence or amount of analytes without the need for a labeled molecule. See, e.g., U.S. Pat. Nos. 5,631,171 and 5,955,377, each of which is hereby incorporated by reference in its entirety, including all tables, figures and claims.

An amplified immunoassay, such as but not limited to, immuno-PCR can also be used. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 1995; 23, S22-529 (1995) or T. Sano et al., in "Molecular Biology and Biotechnology" ed. Robert A. Meyers, VCH Publishers, Inc. (1995), pages 458-460.

Levels of FOXC2 polypeptides may also be determined using protein microarrays. Methods of producing protein microarrays that may be adapted for detecting levels of FOXC2 protein in a clinical sample are described in the art (see for example of Xiao et al. (2005) Mol Cell Endocrinol.; 230(1-2):95-10; Protein Microarrays (2004) Mark Schena (Ed) Jones & Bartlett Publishers, Inc.). U.S. Patent Pub. 2003/0153013 describes methods of detecting proteins, e.g. antigens or antibodies, by immobilizing antibodies in a protein microarray on a membrane and contacting the microarray with detection proteins which can bind to the proteins to form protein complexes. Similarly, U.S. Patent Pub. 2004/0038428 describes methods of constructing protein microarrays.

Alternatively, the level of FOXC2 polypeptide may be detected using mass spectrometric analysis. Mass spectrometric analysis has been used for the detection of proteins in serum samples (see for example Wright et al.(1999) Prostate Cancer Prostatic Dis 2:264-76, and Petricoin et al. (2002) Lancet.; 359 (9306): 572-7). U.S. Patent No. 2003/0013120 describes a system and method for differential protein expression and a diagnostic biomarker discovery system that may be adapted for measuring levels of FOXC2 polypeptides in a fluid sample. Mass spectroscopy methods include Surface Enhanced Laser Desorption Ionization (SELDI) mass spectrometry (MS), SELDI time-of-flight mass spectrometry (TOF-MS), Maldi Qq TOF, MS/MS, TOF-TOF, ESI-Q-TOF and ION-TRAP.

The control can be the level of a FOXC2 gene product in a sample from a normal mammal or the level of FOXC2 gene product in a sample from a mammal having the metastatic condition. If the sample is from a normal mammal, then increased levels of the FOXC2 gene product in the test sample compared with the control indicates that the mammal has an increased risk of developing a metastatic condition as compared with the control. If the sample is from a mammal having the metastatic condition, then similar levels of the FOXC2 gene product in the test sample and the control indicates that the mammal has an increased risk of developing a metastatic condition as compared with the control. Alternatively, the level of the gene product in the test sample can be compared with a standard (e.g., presence or absence of FOXC2 gene product) or numerical value determined (e.g. from analysis of other samples) to correlate with decreased, normal or increased risk of developing a metastatic condition. The advantage of the present invention would be to utilize a more aggressive treatment for a patient at higher risk of a metastatic condition. Correlation can be performed by standard statistical methods such as a Chi-squared test and statistically significant correlations between the regulation of metastasis genes and metastases for a set of individuals which exhibit metastases and a set of individuals which do not.

In one embodiment of the methods described herein, the control level is the level of a FOXC2 gene product in a non-metastatic tumor sample. The control level may be a predetermined standard value, or range of values, (e.g. from analysis of other samples) to correlate with increased risk of having cancer metastasis or of developing cancer metastasis. In one specific embodiment, the control value may be data obtained from a data bank corresponding to nonmetastatic accepted normal levels the FOXC2 gene product under analysis. In situations, such as but not limited to, those where standard data is not available, the methods of the invention may further comprise conducting corresponding analyses in a second set of one or more tumor samples from individuals not having the cancer metastasis, in order to generate the control level. Such additional biological samples can be obtained, for example, from cancer biopsies.

One skilled in the art would appreciate that the control level of FOXC2 gene product may vary according to the type of biological sample, the handling of the biological sample and/or the method used to detect the gene product. For example, prolonged storage of a tumor sample, or repeated freeze-thaw cycles, may result in degradation and loss of detectable signal from a FOXC2 gene product. Likewise, the control level may vary according to the affinity of an antibody for a FOXC2 polypeptide. In one embodiment, the control level is a control level that has been determined using the same type of biological sample, comparable handling of the biological sample, same type of FOXC2 gene product and same detection technique as for the individual being tested.

In the methods of the invention, the comparison of the FOXC2 gene product level with the control level can be a straight-forward comparison, such as but not limited to, a ratio. The comparison can also involve subjecting the measurement data to any appropriate statistical analysis. In the diagnostic procedures of the invention, one or more tumor samples obtained from an individual can be subjected to a battery of analyses in which a desired number of additional genes, gene products, metabolites, and metabolic by-products are measured. In any such diagnostic procedure it is possible that one or more of the measures obtained will produce an inconclusive result. Accordingly, data obtained from a battery of measures can be used to provide for a more conclusive diagnosis and can aid in selection of a normalized control level of FOXC2 expression. It is for this reason that an interpretation of the data based on an appropriate weighting scheme and/or statistical analysis may be desirable in some embodiments.

In another embodiment, abnormal FOXC2 levels are combined with the results of assessment of other risk factors to determine cumulative risk. For example, an individual with a tumor having elevated FOXC2 levels and abnormal level of another gene product indicative of greater metastatic potential, such as CD105 (see Seon et al. (2001) Rinsho Byori.;49 (10):1005-13), isoglobotetraosylceramide (IsoGb4) (see Zhong et al. (2001) Cancer Res.;61(15):5741-8), L-plastin (see Otsuka et al. (2001) Biochem Biophys Res Commun.; 289(4):876-81) or human chorionic gonadotropin (hCG) (see Acebedo et al. (1996) Cancer.;78(11):2388-99). In certain embodiments, assessment of one or more additional markers are combined to increase the predictive value of the analysis in comparison to that obtained from measurement of the FOXC2 gene product alone.

A related aspect of the invention provides a method of predicting the likelihood of development of a metastatic condition in a mammal, comprising the steps of: (a) obtaining a nucleic acid sample from the individual; and (b) determining if the nucleic sample contains at least one mutation in the FOXC2 gene which results in increased FOXC2 expression or activity, wherein the presence of at least one said mutation indicates that the individual is at risk of developing cancer metastasis. In a specific embodiment, determining if the nucleic sample contains mutations in the FOXC2 comprising determining the nucleotide sequence of at least part of the FOXC2 gene. Any number of techniques well known in the art may be used to sequence the FOXC2 gene.

Techniques for determining the presence of particular alleles of FOXC2 would be those known to persons skilled in the art and include, but are not limited to, nucleic acid techniques based on size or sequence, such as restriction fragment length polymorphism (RFLP), nucleic acid sequencing, or nucleic acid hybridization. The nucleic acid tested may be RNA or DNA. These techniques may also comprise the step of amplifying the nucleic acid before analysis. Amplification techniques are known to those of skill in the art and include, but are not limited to, cloning, polymerase chain reaction (PCR), polymerase chain reaction of specific alleles (PASA), polymerase chain ligation, nested polymerase chain reaction, and the like. Amplification products may be assayed in a variety of ways, including size analysis, restriction digestion followed by size analysis, detecting specific tagged oligonucleotide primers in the reaction products, allele-specific oligonucleotide (ASO) hybridization, allele specific exonuclease detection, sequencing, hybridization and the like. Polymorphic variations leading to altered protein sequences or structures may also be detected by analysis of the protein itself. Additional methods for the detection of polymorphisms are described in U.S. Pat. No. 6,453,244 and in International PCT publications No. WO 04/011668, WO 03/048384, WO 01/20031 and WO 03/038125, the teachings of which are hereby incorporated by reference.

Mutations in FOXC2 found in the general population are known in the art, such as those described in Brooks et al., J AAPOS. (2003);7(5):354-7; Yanagisawa et al., Diabetologia. (2003);46(11):1576-80; and Kovacs et al., Diabetes. (2003); 52(5):1292-5. These and other forms of FOXC2 may be tested using any of the assays described herein to determine if a mutation in FOXC2 leads to increased activity or expression.

VI. Methods of Identifying Therapeutic agents

The invention further relates to a method of identifying an agent which regulates metastasis of a tumor cell. Some specific methods comprise the steps of contacting one or more tumor cells with an agent to be tested; and determining the level of a FOXC2 gene product, wherein if the level of the gene product is altered in the presence of the agent as compared with the level of the gene product in the absence of the agent, then the agent regulates metastasis of the tumor cell.

The present invention also provides a method of identifying an agent which inhibits metastasis of a tumor cell, comprising the steps of: contacting one or more tumor cells with an agent to be tested; and determining the level of FOXC2 gene product, wherein if the level of FOXC2 gene product is decreased in the presence of the agent as compared with the level of FOXC2 gene product in the absence of the agent, then the agent inhibits metastasis of a tumor cell.

In an alternate embodiment, the present invention relates to a method of identifying an agent which increases metastasis of a tumor cell, comprising the steps of: contacting one or more tumor cells with an agent to be tested; and determining the level of FOXC2 gene product, wherein if the level of FOXC2 gene product is increased in the presence of the agent as compared with the level of FOXC2 gene product in the absence of the agent, then the agent increases metastasis of a tumor cell.

The step of contacting can be carried out by directly applying the agent to the cell or by combining the agent with a substance which is in contact with the cell (e.g., by administering the agent into cell culture medium). Methods described herein for determining the level of FOXC2 gene expression or the level of a FOXC2 gene product are also useful in the screening methods of the invention.

Any general method known to one skilled in the art may be applied to determine if an agent increases the expression or activity of a FOXC2 gene product. In one specific embodiment for determining if an agent increases the expression of FOXC2, a cell is contacted with an agent, and an indicator of gene expression, such as mRNA level or protein level, is determined. Levels of mRNA may be determined, for example, using such techniques as Northern Blots, reverse-transcriptase polymerase chain reaction (RT-PCR), RNA protection assays or a DNA microarray comprising probes capable of detecting FOXC2 mRNA or cDNA molecules. Likewise, protein levels may be quantitated using techniques well-known in the art, such as western blotting, immuno-sandwich assays, ELISA assays, or any other immunological technique. Techniques for quantitating nucleic acids and proteins may be found, for example, in Molecular Cloning: A Laboratory Manual, 3rd Ed., ed. by Sambrook and Russell (Cold Spring Harbor Laboratory Press: 2001); and in Current Protocols in Cell Biology, ed. by Bonifacino, Dasso, Lippincott-Schwartz, Harford, and Yamada, John Wiley and Sons, Inc., New York, 1999, hereby incorporated by reference in their entirety.

Likewise, any general method known to one skilled in the art may be applied to determining if an agent increases the activity of FOXC2. Activities of FOXC2 include its ability to bind to DNA, to bind to other transcriptional regulators or to promote transcription of target genes. In one embodiment, candidate agents are tested for their ability to modulate FOXC2 activity by (a) providing a system for measuring a biological activity of FOXC2;and (b) measuring the biological activity of FOXC2 in the presence or absence of the candidate compound, wherein a change in FOXC2 activity in the presence of the compound relative to FOXC2 activity in the absence of the compound indicates an ability to modulate FOXC2 activity. In specific embodiments, the biological activity is the ability of FOXC2 to bind the promoter of a target gene, such as the promoter of lipoprotein lipase (Kamei et al., FEBS Lett. (2003)536(1-3):232-6), which may be determined using chromatin immunoprecipitation and analysis of the DNA bound to an FOXC2 polypeptide.

In another embodiment, the biological activity is promoting transcription of a target gene. An indicator of gene expression for a target gene whose transcription is regulated by FOXC2 or can be compared between cells which have or have not been contacted with the agent. In specific embodiments, FOXC2 transcriptional coactivators are also present when testing of an agent modulates the transcriptional activating activity of a FOXC2 polypeptide.

One particular embodiment for identifying agents which modulate activity of FOXC2 employs two genetic constructs. One is typically a plasmid that continuously expresses the transcriptional regulator of interest when transfected into an appropriate cell line. The second is a plasmid which expresses a reporter, e.g., luciferase under transcriptional control of FOXC2. For example, if a compound which acts as an activator of FOXC2 is to be evaluated, one of the plasmids would be a construct that results in expression of FOXC2 in a cell line. The second would possess a promoter linked to the luciferase gene in which an FOXC2 response element is inserted. If the compound to be tested is an agonist for the FOXC2, the compound may complex with FOXC2 and the resulting complex binds the response element and initiates transcription of the luciferase gene. In time the cells are lysed and a substrate for luciferase added. The resulting chemiluminescence is measured photometrically. Dose response curves are obtained and can be compared to the activity of known ligands. Other reporters than luciferase can be used including CAT and other enzymes. Viral constructs can be used to introduce the gene for FOXC2 and the reporter into a cell. An usual viral vector is an adenovirus. For further details concerning this preferred assay, see U.S. Pat. No. 4,981,784 issued Jan. 1, 1991 hereby incorporated by reference, and Evans et al., WO88/03168 published on 5 May 1988, also incorporated by reference. FOXC2 antagonists can be identified using this same basic "agonist" assay. A fixed amount of an antagonist is added to the cells with varying amounts of test compound to generate a dose response curve. If the compound is an antagonist, expression of luciferase is suppressed.

Additional methods for the isolation of agonists and antagonist of transcriptional regulators are described in U.S. Pat. Nos. 6,187,533; 5,620,887; 5,804,374; and 5,298,429, and U.S. Patent Publication Nos. 2004/0033942A1, 2003/0077664, 2003/0215829 and 2003/0039980. Any of the methods described herein may be easily adapted to identify agonists or antagonists of FOXC2 polypeptides.

The invention also provides a method for screening a candidate compound for its ability to modulate FOXC2 activity in a suitable system, in the presence or absence of the candidate compound. A change in FOXC2 activity in the presence of the compound relative to FOXC2 activity in the absence of the compound indicates that the compound modulates FOXC2 activity. FOXC2 activity is increased relative to the control in the presence of the compound, the compound is an FOXC2 agonist. Conversely, if FOXC2 activity is decreased in the presence of the compound, the compound is an FOXC2 antagonist.

Another way of determining if an agent increases the activity of FOXC2 may also be based on binding of the agent to an FOXC2 polypeptide or fragment thereof. Such competitive binding assays are well known to those skilled in the art. Once binding has been established for a particular agent, a biological activity assay is employed to determine agonist or antagonist potential.

For example, the invention provides screening methods for compounds able to bind to FOXC2 which are therefore candidates for modifying the activity of FOXC2. Various suitable screening methods are known to those in the art, including immobilization of FOXC2 on a substrate and exposure of the bound FOXC2 to candidate compounds, followed by elution of compounds which have bound to the FOXC2.FOXC2 peptides and FOXC2 polypeptides can be immobilized on any solid matrix, such as a plate, a bead or a filter. The peptide or polypeptide can be immobilized on a matrix which contains reactive groups that bind to the polypeptide. Alternatively or in combination, reactive groups such as cysteines in the protein can react and bind to the matrix. In another embodiment, the polypeptide may be expressed as a fusion protein with another polypeptide which has a high binding affinity to the matrix, such as a fusion protein to streptavidin which binds biotin with high affinity.

A variety of assay formats will suffice and, in light of the present disclosure, those not expressly described herein will nevertheless be comprehended by one of ordinary skill in the art. Assay formats which approximate such conditions as formation of protein complexes, enzymatic activity, may be generated in many different forms, and include assays based on cell-free systems, e.g. purified proteins or cell lysates, as well as cell-based assays which utilize intact cells. Simple binding assays can also be used to detect agents which bind to FOXC2. Such binding assays may also identify agents that act by disrupting the interaction between a FOXC2 and a FOXC2 interacting protein. Agents to be tested can be produced, for example, by bacteria, yeast or other organisms (e.g. natural products), produced chemically (e.g. small molecules, including peptidomimetics), or produced recombinantly. Because FOXC2 polypeptides contain multiple domains, specific embodiments of the assays and methods described to identify agents which modulate FOXC2 activity employ fragments of FOXC2 rather than full-length polypeptides, such as those lacking the DNA binding domains. Fragments of FOXC2 may also be used in some embodiments, and in particular fragments which retain at least one biological activity of FOXC2.

In many drug screening programs which test libraries of compounds and natural extracts, high throughput assays are desirable in order to maximize the number of compounds surveyed in a given period of time. Assays of the present invention which are performed in cell-free systems, which may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test agent can be generally ignored in the in vitro system, the assay instead being focused primarily on the effect of the drug on the molecular target as may be manifest in an alteration of binding affinity with other proteins or changes in enzymatic properties of the molecular target.

In specific embodiments, the cells used in the methods described herein for identifying agents are cells in culture or from an individual, such as a tissue, fluid or organ or a portion of any of the foregoing.

Agents identified using the methods of the present invention maybe further tested in model systems for their efficacy in inducing the desired biological response or in treating disorders. For example, U.S. Pat. Nos. 6,251,384 and 6,235,967 describes methods and models for assaying the effectiveness of a candidate metastasis inhibiting compound. U.S. Publication No. 2003/0005470, published Jan. 2, 2003, describes a nonhuman bone-metastasis animal system.

One aspect of the invention provides a method of determining if an agent is a potential agent for the treatment of a hyperplastic disorder, the method comprising determining if the agent decreases the expression or, activity of FOXC2 in a cell, wherein an agent that decreases the expression or activity of FOXC2 is a potential target for the treatment of the disorder. In a specific embodiment, determining if the agent decreases the expression of FOXC2 in a cell comprises (a) contacting the cell with the agent; (b) determining a measure of FOXC2 expression; and (c) comparing the measure of FOXC2 expression to an appropriate control. In another specific embodiment, determining a measure of FOXC2 expression comprises (a) determining FOXC2 mRNA levels or FOXC2 polypeptide levels; or (b) determining the activity of the FOXC2 promoter. In another specific embodiment, the cell comprises a recombinant nucleic acid comprising a FOXC2 promoter operably linked to a reporter gene. In yet another embodiment, the appropriate control comprises a measure of FOXC2 expression in a cell that is not contacted with the agent.

In one embodiment of the methods of determining if an agent is a potential agent for the treatment of a hyperplastic disorder, determining if the agent decreases the activity of FOXC2 in a cell comprises (a) contacting the cell with the agent; (b) determining a measure of FOXC2 activity; and (c) comparing the measure of FOXC2 activity to an appropriate control. In a specific embodiment, a measure of FOXC2 activity comprises FOXC2 transcriptional activating activity. In another specific embodiment, the determining a measure of FOXC2 activity comprises determining the expression level of a gene whose transcription is regulated by FOXC2. In yet another specific embodiment of this method, the cell comprises a recombinant nucleic acid comprising a promoter, which is transcriptionally regulated by FOXC2, operably linked to a reporter gene.

It is well understood by one skilled in the art that many of the methods described herein may be carried out using variants of the polypeptides described. Variants include truncated polypeptides, mutant polypeptides, such as those carrying point mutations, and fusions between domains of the individual polypeptides and other polypeptides. In some embodiments, the individual polypeptides, or their domains, may be fused to reporter proteins, such as to GFP or to enzymes.

In some embodiments of any of the methods described herein, the polypeptides used are 50, 60, 70, 80, 90, 95, 98 or 99% identical to the sequences referenced to in the various Genbank Accession numbers.

In some embodiments of the methods described herein for determining if an agent is a potential agent for the treatment of tumor metastasis, the method further comprises administering the agent to an animal having a tumor, and determining if the tumor metastasizes in the animal. In some embodiments, the animal is a mammal. Any tumor metastasis assay known to one skilled in the art may be used in the animal. In one embodiment, a spontaneous metastasis assay may be used. As a nonlimiting illustrative example, $0.5 \times 10^6$ tumor cells in 0.2 ml of PBS may be injected subcutaneously into the dorsal flank of 5-week-old SCID2 mice (Harlan Sprague-Dawley, Indianapolis, Ind.). Mice may be monitored daily, and the tumor volume measured as an index of the growth rate. Mice may be sacrificed 2-6 weeks after the inoculation of the cells, and metastatic lesions on the lungs may be counted macroscopically. In another embodiment, a tail vein metastasis assay may be used. As a nonlimiting illustrative example, a metastatic amelanotic melanoma cell line may be cultured and injected intravenously with $10^6$ cells in 0.1 ml of DMEM via the tail vein. Mice may be euthanized 21, 28, and 35 days after injection and examined grossly at necropsy for the presence of metastases in internal organs. Microscopic quantitation of metastases may be performed on representative cross sections of formalin-fixed, paraffin-embedded tissue stained with hematoxylin and eosin.

Exemplification

The invention now being generally described, it will be more readily understood by reference to the following examples, which are included merely for purposes of illustration of certain aspects and embodiments of the present invention, and are not intended to limit the invention, as one skilled in the art would recognize from the teachings herein above and the following examples, that other, cell types, agents, assay systems, constructs, or data analysis methods, all without limitation, can be employed, without departing from the scope of the invention as claimed.

The contents of any patents, patent applications, patent publications, or scientific articles referenced anywhere in this application are herein incorporated by reference in their entirety.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003.

RESULTS

Summary of Experimental Results

FOXC2 is a member of winged helix forkhead family transcription factors, which has been shown to be involved in embryogenesis and metabolism. Applicants identified FOXC2 being overexpressed specifically in highly metastatic cancer cell lines. Suppression by Applicants of the expression of FOXC2 in the highly metastatic 4T1 cells blocked the metastasis. In accordance with this observation, overexpression by Applicants of FOXC2 in non-metastatic cells induced metastasis indicating that FOXC2 modulates at least one of the several steps of metastasis. Applicants observed that FOXC2 can induce an EMT, increase migration and invasion, and promote secretion of MMPs that are necessary for the tissue remodeling.

However, unlike other EMT-inducing transcription factors associated with mesoderm development, FOXC2 is unable to effectively repress the expression of epithelial markers. In one model, transcription factors such as Snail, Twist and Slug may directly repress E-Cadherin and then they activate FOXC2 to induce many of the mesenchymal traits associated with the EMT. FOXC2 is induced by TGF-β1 and, at the same time, reinforces its expression, suggesting that it plays an important role in TGF-β1-induced invasion and metastasis. Importantly, expression of FOXC2 in the highly aggressive ER-negative tumors with poor outcome suggests that expression of this gene could be used as a prognostic marker along with other markers.

Migration of cancer cells during cancer metastasis mimics embryogenesis. Several developmentally important genes reported to play an important role in cancer metastasis. Applicants have identified FOXC2, member of the forkhead family gene as a candidate metastatic gene in our screen. Suppression of the expression of FOXC2 in highly metastatic mammary carcinoma cells blocked its metastatic abilities. Likewise, overexpression of FOXC2 in poorly metastatic mammary carcinoma cells enhances the metastatic ability of breast carcinoma cells. Mechanistically, FOXC2 induces epithelial cells to undergo an epithelial-mesenchymal transition (EMT), as well as inducing them to become motile and invasive. Moreover, FOXC2 expression is induced by all known activators of the EMT, such as TGF-fβ1, Ras, Snail, and Twist indicating that it could be a central player in this process. Most importantly, FOXC2 is aberrantly expressed in a highly aggressive subtype of breast cancer termed "basal-like breast cancer", which constitute 15% of all breast cancer for which it proves to be a highly specific molecular marker. Taken together, these observations indicate that FOXC2 plays a central role in promoting invasion and metastasis.

Experimental Procedures

Cell lines: The mouse mammary tumor cell lines, 67NR, 168FARN, 4TO7 and 4T1, human mammary epithelial cell line-HMEC and MDCK cell lines were maintained as described.

Microarray hybridization, data collection and data analysis, SYBR-Green Real-time RT-PCR, data analysis, and immunofluorescence methods are described in reference 2.

Metastasis assay: EpRas-pBp and pBp-FOXC2 cells were injected either subcutaneously ($5\times10^5$ and $1\times10^5$) into female nude mice. Five to six weeks later, the mice were sacrificed and analyzed for the number of metastatic nodules in the lung under the dissection microscope.

Antibodies and Western Blotting: Monoclonal FOXC2 antibody was originally reported by Naoyuki Miura. The other antibodies utilized were anti-β-actin (Abcam), anti-E-cadherin (BD Transduction), anti-α-catenin (BD Transduction), anti-γ-catenin (BD Transduction), anti-γ-catenin (BD Transduction), anti-Fibronectin (BD Transduction), anti-vimentin V9 (NeoMarkers), anti-N-cadherin (BD Transduction), anti-smooth muscle actin (Sigma). All cells were lysed in the presence of 50 mM Tris PH 7.5, 150 mM NaCl and 0.5% NP-40 for 30 minutes on ice. The samples were spun at 14,000 RPM at 4° C. for 10 minutes. The supernatants were collected and measured for protein concentration. 25-100 µg total protein for each samples were separated on a 4-14% Bis-Tris Gel with MOPs Running Buffer and transferred to PVDF membranes following the manufacturer's instruction (Invitrogen).

Migration assay: Cell migration assays were performed using 8.0 µm pore size Falcon Cell Culture Insert System (Falcon). $5\times10^4$ cells were seeded on the insert in 250 ul growth factor-free media. Inserts were placed into the 24-well companion plate with 750 ul DME, 40 hours later, the remaining cells on the upper chambers of the inserts were cleaned with Q-tips. The inserts were fixed with 4% paraformaldehyde, stained with Crystal violet and dried. The total number of cells migrated through the 8.0 µm membrane were counted. The migration of each cell line was measured in triplicate and error bars represent the standard error of the mean. For the invasion assay, the inserts were coated with Matrigel and essentially followed the same protocol. ELISA: MMP-2 (cat #—QIA63), MMP-9 (cat #—QIA56) from Oncogene Research Products and TGF-β1 (cat #—G7590) from Promega were used following the manufacturer's protocol.

Human breast tumor tissue array: Two tissue microarrays of primary human breast tumors were available for a cohort of 117 cases for which tumor subtype had been determined by hierarchical clustering analysis of gene expression profiles. (Supplemental data). Histologic tumor grade, estrogen receptor immunohistochemistry, and HER-2 immunohistochemistry pathology annotation were available for each case. This cohort consisted of 18 tumors in the basal-like cluster, 34 tumors in the HER-2 positive cluster, and 65 ER-positive tumors from two combined luminal clusters. Tissue arrays contained two representative 0.6 mm cores of each tumor and representative cores of normal breast tissues.

Figure 1:
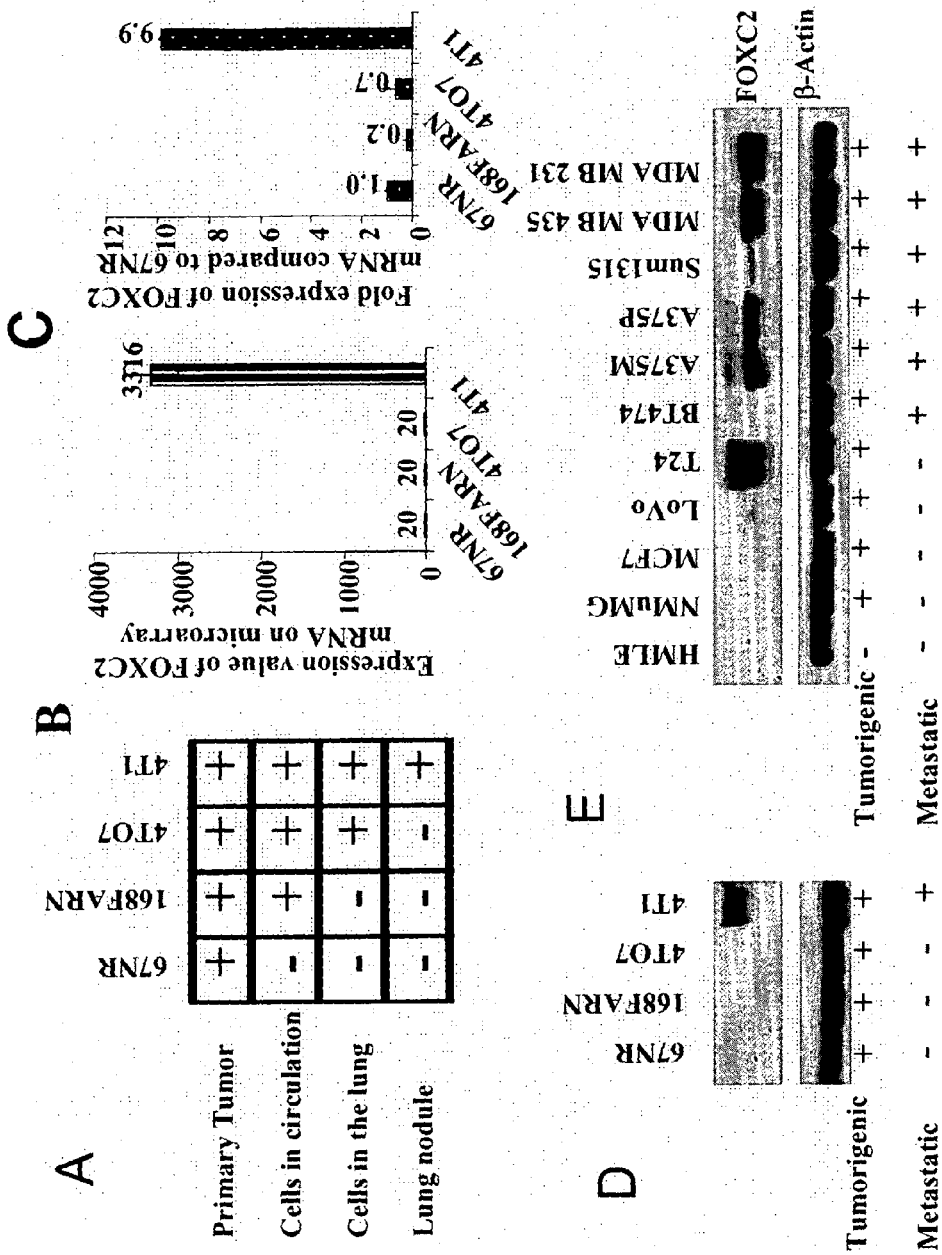
FIGS. 1A-1E show that FOXC2 is specifically expressed in highly metastatic cell lines.

Immunohistochemistry: Immunohistochemistry was performed using 5.0 micron thick formalin-fixed, paraffin-embedded tissue microarray sections. Briefly, slides were successively soaked in xylene for at least 2 hours, passed through graded alcohols and, put in distilled water. Slides were then pre-treated with 10-mM citrate, pH 6.0 (Zymed, South San Francisco, Calif.) in a steam pressure cooker (Decloaking Chamber, BioCare Medical, Walnut Creek, Calif.) per manufacturers instructions followed by washing in distilled water. All further steps were performed at room temperature in a hydrated chamber. Slides were pre-treated with Peroxidase Block (DAKO USA, Carpinteria, Calif.) for 5 minutes to quench endogenous peroxidase activity and blocked with 20% goat serum for 20 minutes to prevent non-specific protein binding. Primary murine anti-human FOXC2 antibody was applied at a 1:200 dilution in DAKO diluent for 1 hour. Slides were washed in 50-mM Tris-Cl, pH 7.4, and anti-murine horseradish peroxidase-conjugated antibody (Envision detection kit, DAKO) was applied for 30 minutes. After further washing, immunoperoxidase staining was developed using a DAB chromogen kit (DAKO) per the manufacturer and counterstained with hematoxylin. Immunoreactivity was scored as "Low" for absent or weak cytoplasmic staining, "Moderate" for intermediate cytoplasmic staining or "High for strong cytoplasmic staining or nuclear staining (FIG. 1F).

Experiment 1

Metastasis is the migration of cancer cells from their primary tumor site to secondary sites where they then invade normal tissue and begin to proliferate and form new tumors. The molecular mechanism of migration of cells during development and metastasis is similar but the regulation is disturbed in metastasis. A number of genes have been identified being responsible for cancer metastasis. Most of these genes are expressed in tumor at high level compared to normal tissues. So targeting such genes for therapy is difficult. The ideal gene for therapy would be the one, which is not expressed in normal adult tissues but specifically expressed in metastatic tumors.

To identify such genes capable of modulating cancer invasion and metastasis, Applicants analyzed the gene expression patterns of tumors formed by four murine mammary carcinoma cells lines (67NR, 168FARN, 4T07 and 4T1) with differing metastatic abilities. The properties of these lines are summarized in FIG. 1A and in earlier reports. The first of these (67NR) is capable of forming only primary carcinomas, while the second (168FARN) can disseminate cells to the blood stream as well; the third (4T07) can induce the formation of micrometastases, while the fourth (4T1) can execute all the steps required for the formation of macroscopic metastases. Using expression microarrays, Applicants identified a set of genes that were differentially expressed between the tumors formed by these various cells. Methods of data collection and analysis and the list of differentially expressed genes have been previously reported. These analyses revealed that the FOXC2 gene is expressed only in the 4T1 cell line, which is capable of completing all steps of metastasis, but not in the other lines. (FIG. 1B). To validate the microarray results, Applicants performed real time PCR reactions on RNAs extracted from the tumors. Only tumors generated by 4T1 cells expressed FOXC2 mRNA (FIG. 1C). Similarly, expression of FOXC2 protein was detectable only in the 4T1cells by western blotting (FIG. 1D). To determine whether FOXC2 expression correlates with the metastatic abilities of certain tumors, Applicants screened a number of established metastatic and non-metastatic cell-lines derived from mouse and human tissues for the expression of FOXC2.FOXC2 protein was expressed in seven of nine metastatic lines, but only in one out of four non-metastatic lines. No expression was detected in non-transformed immortalized human mammary epithelial cells (HMLE) (FIG. 1E). This correlation encouraged us to characterize the role of FOXC2 in cancer cell invasion and metastasis.

Experiment 2

To test whether FOXC2 is necessary for the metastasis of 4T1 cells, Applicants constructed short hairpin oligos against FOXC2 and tested for suppression of expression by stably introducing them to the 4T1 cells. Out of 15 oligos tested, one blocked the expression completely (SiFOXC2-14) and the second one blocked partially (SiFOXC2-7) compared to the control oligo (SiLamin) (FIG. 2A). In vitro, cells expressing the SiFOXC2-14 had reduced cell growth compared to the control SiLamin oligos (FIG. 2B). To test whether there will be any difference in the growth rate in vivo and to test the role in metastasis, Applicants injected these cells in vivo at the orthotopic site mammary fatpad. Applicants harvested the tumor after 21 days and 28 days, measured the tumor weight (FIG. 2C) and the visible tumor nodules in the lung (FIG. 2D, E). Similar to in vitro, SiFOXC2-14 cells grew slower compared to the control (FIG. 2C) whereas the SiFOXC2-7 cells .grew similar to the control cells (FIG. 2C) at day 28. Whereas at day 21, all three type of cells formed tumor at similar rate and the tumor weight is also similar at the end time point. However, the SiFOXC2-14 and 7 cells formed very few visible nodules compared to the control cells at both time points (FIG. 2D, E). Applicants speculated that the colonies found in the SiFOXC2 cells are due to loss of suppression in the 4T1 cells. Applicants cultured the tumor cells from the lung nodules of SiFOXC2-7 and SiFOXC2-14 cells carrying mice along with control oligo (Si-Lamin). These cells had turned on the FOXC2 expression compared to the cells from the primary tumor therefore they formed colonies in the lung. All these results suggest that FOXC2 is necessary for metastasis.

Experiment 3

Since Applicants identified FOXC2 in the highly metastatic cell line 4T1, it is likely that overexpression of this gene in the weakly metastatic 4TO7 cells may promote metastasis. So, Applicants tried to overexpress FOXC2 in the poorly metastatic 4TO7 cells, however Applicants could not get 4TO7 cells infected with retrovirus since they had endogenous retrovirus. So Applicants chose to use another mouse mammary cancer cell line EpRas, which is reported to be a non-metastatic. Applicants ectopically expressed FOXC2 in EpRas cells using retrovirus and confirmed its expression (FIG. 3A). There was no significant difference in the growth rate in vitro compared to the control cells. Applicants injected these cells at the subcutaneous site of the nude mouse and monitored the tumor growth. Ectopic expression of FOXC2 did not affect the kinetics of primary tumor formation by these cells (FIG. 3B) however the control EpRas cells gave rise to 13($\pm$2) metastatic nodules per lung in contrast to tumors formed by FOXC2-expressing cells, which gave rise to ~40($\pm$12) metastatic nodules per lung (FIG. 3C) suggesting that FOXC2 function is specifically associated with the capability of tumors to metastasize (FIG. 3B). The level of FOXC2 protein in the primary tumors correlated with the number of nodules formed in the lungs of the tumor-bearing mice, that is, tumor expressing higher levels of FOXC2 formed more metastatic nodules (FIG. 3D, F). These results indicate that FOXC2 can, on its own, contribute significantly to the metastatic phenotype of mammary carcinoma cells.

Experiment 4

To understand the mechanism by which FOXC2 induce metastasis, Applicants explored the function of FOXC2.During embryogenesis, FOXC2 expression is restricted to the mesoderm and mesoderm derived tissues and is therefore proposed to play an important role in establishing and maintaining the differentiation of mesodermal tissues during development. In adult, FOXC2 expression is restricted to adipose tissues. During development, mesodermal tissues are generated from epithelial cells by a process called Epithelial to Mesenchymal Transition (EMT) and acquire migratory characteristics. Similar to development, EMT is also propose to play an important role in metastasis in converting the epithelial cancer cells to become mesenchymal and facilitate the migration from one tissue to another. Several genes capable of inducing mesoderm during embryogenesis is also capable of inducing EMT thereby promote metastasis. Applicants therefore hypothesized that FOXC2 might affect the differentiation characteristics of epithelial cells and probably induce epithelial-mesenchymal transition (EMT). Applicants analyzed the EpRas cells for the expression of EMT associated markers and Applicants not see any difference in the expression of markers associated with EMT in the cells expressing FOXC2. This could be due to inefficiency of FOXC2 alone to induce EMT since, EpRas cells has been reported to undergo EMT in vivo in response to TGF-beta 1. Based on the embryogenesis data, Applicants hypothesized that FOXC2 will be capable of inducing EMT and EpRas may not be the right cell line to test this. Therefore Applicants overexpressed FOXC2 in a number of epithelial cells such as MCF7, T47D, MCF-10A, HMLE (immortalized human mammary epithelial cells), NMuMG, and MDCK cells. Unfortunately, FOXC2 induced cell death in every cell line tested except MDCK (Kidney epithelial cells) cells. Interestingly, overexpression of FOXC2 in MDCK cells using retrovirus (FIG. 4A), resulted in loss of their cuboidal epithelial morphology, acquisition of a spindly, elongated morphology, and loss of cell-cell adhesion (FIG. 4B). These changes are indicative of an EMT.

Experiment 5

The ability of carcinoma cells to migrate and invade the surrounding environment are critical initial steps in invasion and metastasis. Applicants performed Boyden-chamber transwell-assays in order to determine whether ectopic expression of FOXC2 in MDCK cells could induce these phenotypes. FOXC2 overexpression rendered MDCK cells highly motile in comparison to control cells and capable of invading through Matrigel-coated membranes (FIG. 4F). These results suggest that FOXC2 is indeed capable of modulating the migration and invasion of cancer cells. Applicants therefore analyzed for changes associated to EMT.

Ectopic expression of FOXC2 in MDCK cells induced the expression of vimentin, fibronectin, N-cadherin and, α-smooth-muscle actin, all mesenchymal markers typically induced during EMT. Expression of epithelial markers, such as E-cadherin, a-catenin, and γ-catenin was partially down-regulated, while expression of β-catenin was unchanged (FIG. 4C, D, E). These results indicate that FOXC2 can induce an EMT in MDCK cells. However, the phenotypic change induced by FOXC2 does not involve the complete shutdown of epithelial markers, which does occur upon the overexpression of other EMT inducing transcription factors, such as Twist, Snail, Slug, E12/E47 and SIP1. Since there is no complete shutdown of E-Cadherin and change of morphology, Applicants were interested to test the localization of FOXC2 in the cells expressing FOXC2 and found out that the E-Cadherin is localized within the cells and not in the membrane suggesting that overexpression of FOXC2 somehow delocalize E-cadherin and brings out the change in morphology. Applicants are in the process of investigating this further. This result also supports why Applicants didn't see an EMT in EpRas cells and suggests that FOXC2 is primarily associated with the induction of mesenchyme-specific genes, while other transcription factors, such as Snail, Twist and Slug are involved in repressing epithelium-specific genes and inducing mesenchymal markers.

Experiment 6

In order for cells to become invasive, they must degrade the extracellular matrix (ECM). This process is facilitated by production of matrix metalloproteinases (MMPs) such as MMP9 and MMP2. In fact, as gauged by ELISA, Applicants found MMP2 and MMP9 to be strongly induced in response to the expression of FOXC2 in MDCK cells (FIG. 4G) compared to the level expressed in the control MDCK cells. Together, these observations indicate that FOXC2 is capable of acting pleiotropically to induce many of the cellular phenotypes that are associated with invasion and metastasis.

FOXC2 upregulates mesenchymal markers in MDCK cells and is known to induce differentiation in mesodermal tissues during development. Applicants speculated that FOXC2 might be used by other EMT-inducing transcription factors to regulate the mesenchymal component of the EMT program. Applicants therefore ectopically expressed Snail, Twist and an activated form of the Ras oncoprotein independently in HMLE cells. In accord with previous reports, the ectopic expression of each of these proteins induced an EMT in these cells (FIG. 4H-i). Similarly Applicants also treated HMLE cells with TGF-beta land observed EMT (FIG. 4H-ii) interestingly; Applicants observed that the expression of the endogenous FOXC2 gene was also activated by all four activators of EMT at the RNA (FIG. 4I-i, ii) and protein levels (FIG. 4I-iii). However FOXC2 is not expressed in three different isolates of human mammary fibroblasts (FIG. 4I-iv). Taken together with earlier observations described above, these results indicate that expression of FOXC2 is tightly associated with EMT and suggest that FOXC2 could be a central regulator of the EMT program and is used by other EMT-inducing transcription factor to orchestrate a critical part of this program.

Experiment 7

Figure 4J:
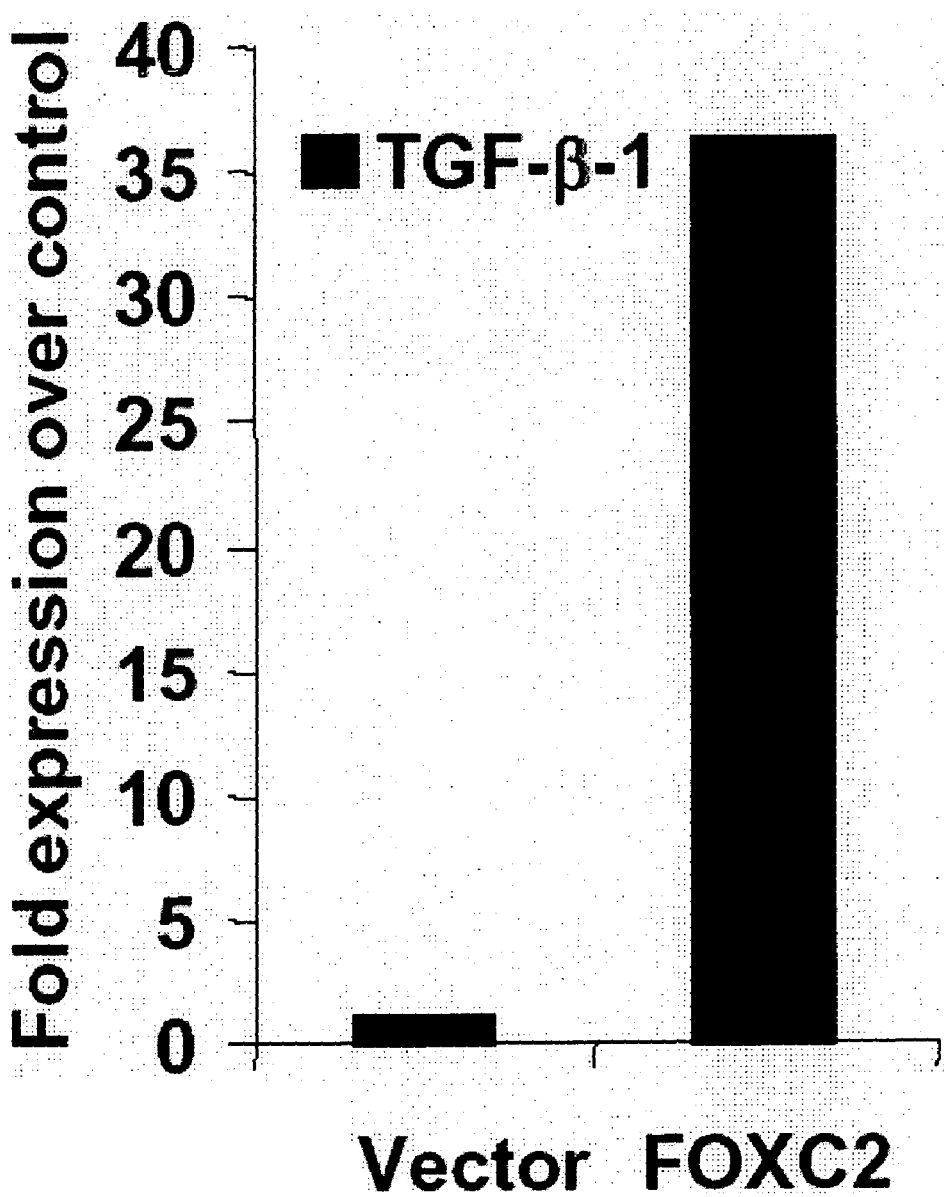

Apart from inducing the mesenchymal markers, FOXC2 could help maintain the EMT state by inducing TGF-β1 expression, thereby generating a positive feedback loop to reinforce this phenotype. Applicants therefore set out to test whether TGF-β1 is induced by FOXC2 in MDCK cells. Indeed, expression of TGF-β1 is induced in MDCK cells upon expression of FOXC2 compared to control cells (FIG. 4J). These and the earlier results indicate that FOXC2 expression is induced by TGF-β exposure and, at the same time, can promote expression of TGF-β, suggesting that it may play a key role in maintaining EMT in certain cell types.

Experiment 8

In order to test whether FOXC2 is involved in human tumorigenesis, Applicants analysed the dataset generated from 117 primary invasive human breast carcinoma samples. These tumors have been categorized into subtypes on the basis of their gene expression profiling (shown in FIG. 6). Applicants could not detect any mRNA signal for FOXC2 using the data generated by microarray. Applicants then performed immunohistochemistry using FOXC2 antibody on a set of normal breast tissue sections and on tissue microarrays containing samples of 117 primary invasive breast carcinomas. No significant expression of FOXC2 was detected in normal breast tissue from reduction mammoplasties (FIG. 5A). In contrast, FOXC2 expression was detectable in 85% of invasive carcinomas. The immunoreactivity pattern ranged from absent (FIG. 5B), to faint cytoplasmic staining (low, L) in 52% of cases (FIG. 5C), moderate cytoplasmic staining (moderate, M) in 37% (FIG. 5D), and strong cytoplasmic and/or nuclear staining (high, H) in 10% (FIG. 5E, F). In several cases of the basal-like breast carcinoma, intense staining of FOXC2 was detected for FOXC2 both in the cytoplasm and in the nucleus of cancer cells, shown at higher magnification. Applicants found that high level of FOXC2 expression was associated with several adverse prognostic markers including ER-negativity (p-value-3.17e-006), high tumor grade (p-value-0.00126), and, interestingly, with the aggressive basal-like tumor subtype (p-value-1.02e-006) (FIG. 5G, H). 44% of basal-like tumors showed high levels of FOXC2 expression, whereas only 8% of HER-2 positive tumors and 1% of luminal ER+ tumors showed high expression (FIG. 5G, H). The basal-like subtype of breast cancer has been reported in multiple studies to be highly aggressive with the worst long-term outcome due to the recurrence of distant metastases.

A model of metastasis is shown in FIG. 7.

We claim:

1. A method for predicting the likelihood that the tumor in an individual will metastasize, the method comprising
   (a) determining the level of a Forkhead Box C2 (FOXC2) gene product in a sample obtained from the tumor of the individual; and
   (b) comparing the level with a control level of FOXC2 expression from a non-metastatic tumor sample,
   wherein if the level determined in (a) is greater than the control level, the individual is said to have increased likelihood of the tumor metastasizing.

2. A method of predicting the likelihood of development of a tumor metastasis in an individual, comprising the steps of:
   (a) obtaining a tumor sample from the individual to be tested;
   (b) determining the level of a Forkhead Box C2 (FOXC2) gene product in the tumor sample; and
   (c) comparing the level determined in (b) with a control level of FOXC2 expression from a non-metastatic tumor sample,
   wherein if the level determined in (b) is greater than the control level, then the individual has an increased likelihood of developing a metastatic condition.

3. The method of claim 2, wherein the FOXC2 gene product is a FOXC2 polypeptide or a FOXC2 mRNA.

4. The method of claim 2, wherein determining the level of the FOXC2 gene product in the biological sample comprises determining the bioactivity of a FOXC2 polypeptide in the sample.

5. The method of claim 2, further comprising determining the level of at least one additional gene product in the sample that is indicative of metastasis.

* * * * *